(12) United States Patent
Alam et al.

(10) Patent No.: US 10,041,894 B1
(45) Date of Patent: Aug. 7, 2018

(54) THERMAL CONDUCTIVITY MEASUREMENT OF ANISOTROPIC SUBSTRATES

(71) Applicant: Amazon Technologies, Inc., Seattle, WA (US)

(72) Inventors: Mohammed Aftab Alam, San Jose, CA (US); Bradley David Urban, Cupertino, CA (US); Gaurav Soni, Fremont, CA (US); Ramez Nachman, San Francisco, CA (US)

(73) Assignee: Amazon Technologies, Inc., Seattle, WA (US)

( * ) Notice: Subject to any disclaimer, the term of this patent is extended or adjusted under 35 U.S.C. 154(b) by 264 days.

(21) Appl. No.: 14/849,471

(22) Filed: Sep. 9, 2015

(51) Int. Cl.
*G01N 25/18* (2006.01)

(52) U.S. Cl.
CPC .................................. *G01N 25/18* (2013.01)

(58) Field of Classification Search
None
See application file for complete search history.

(56) References Cited

U.S. PATENT DOCUMENTS

2009/0146676 A1* 6/2009 Zogmal ............... F25D 19/006
324/750.08

2012/0294329 A1* 11/2012 Miller ..................... G01N 25/18
374/44
2014/0016664 A1* 1/2014 Pauchet ................ G01N 25/18
374/44

OTHER PUBLICATIONS

Miettinen, "In-Plane Conductive Heat Transfer in Solid and Porous Planar Structures," Dec. 2011, 74 pages.
Researchgate.net, "What is the significance of in-plane and through plane conductivity of thermoplastic materials?" retrieved on Feb. 22, 2018 from <<https://www.researchgate.net/post/What_is_the_significance_of_in-plane_and_through_plane_conductivity_of_thermosplastic_materials>> 2 pages.

* cited by examiner

*Primary Examiner* — Erica Lin
(74) *Attorney, Agent, or Firm* — Lee & Hayes, PLLC

(57) ABSTRACT

Determining an in-plane thermal conductivity of anisotropic materials, such as display stacks, printed circuit boards (PCBs), and composite housings, includes heating a first region of an anisotropic sample, cooling a second region of the sample, and measuring temperature at a first location between the first region and the second region and a second location between the first region and the second region. The in-plane thermal conductivity of the sample is computed based at least in part on the temperature at the first location, the temperature at the second location, the distance from the first region to the second region, a thickness of the substantially planar anisotropic substrate, and an amount of heat applied to the first region.

20 Claims, 15 Drawing Sheets

US 10,041,894 B1

THERMAL CONDUCTIVITY MEASUREMENT OF ANISOTROPIC SUBSTRATES

BACKGROUND

Electronic devices come in many different shapes and sizes. Advances in technology result in ever more powerful electronic devices (in terms of processing power, storage, and battery life). As electronic devices become more powerful, they tend to generate more heat. For example, processors, wireless transceivers, and display screens all generate heat. Additionally, electronic devices are used in a multitude of environments and activities. Such environments and activities expose electronic devices to a wide range of environmental temperatures.

If electronic devices get too hot or too cold, performance may degrade (e.g., they may become less efficient), components may become damaged, and/or surfaces may become uncomfortable to hold or operate. Thus, designers typically design electronic devices to minimize their exposure to extreme temperatures. To do this, designers rely on knowledge of thermal conductivity characteristics of various materials. However, existing thermal measurement techniques are unable to measure thermal conductivity of certain components.

BRIEF DESCRIPTION OF THE DRAWINGS

The detailed description references the accompanying figures. In the figures, the left-most digit(s) of a reference number identifies the figure in which the reference number first appears. The use of the same reference numbers in different figures indicates similar or identical items.

DETAILED DESCRIPTION

Figure 1:
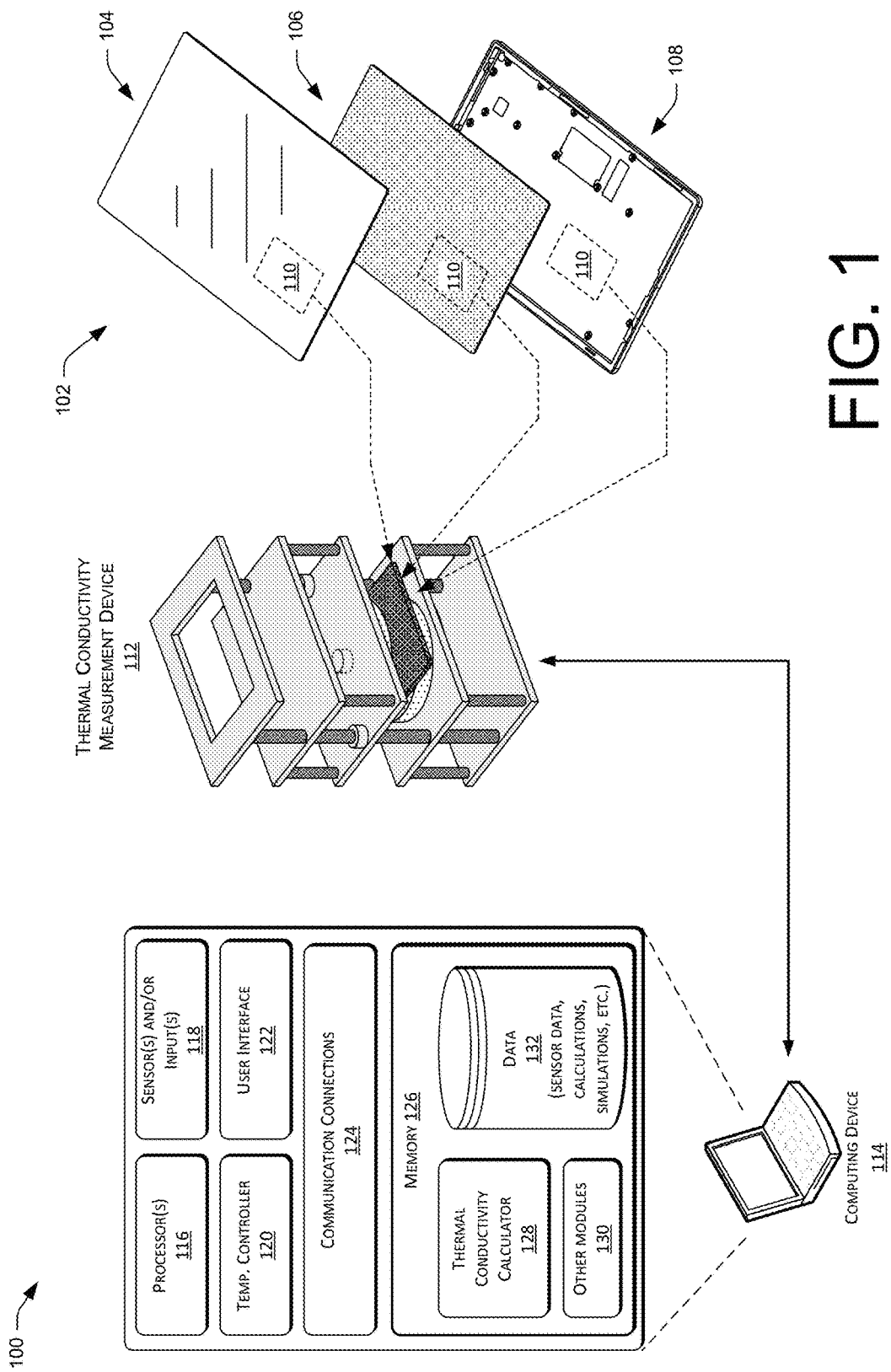
FIG. 1 is a schematic view of an example system usable for measuring in-plane and/or out of plane thermal conductivity of a sample.

Electronic device designers often use thermal simulations during the design process to determine how hot a device will get during various use conditions. To do this, designers use the thermal conductivity (k) of each material of the electronic device. Thermal conductivity is a material constant and for an isotropic material can be defined by the following equation:

$$k = (Q\Delta x) \div A(T_2 - T_1) \quad (1)$$

where Q is the heat flow, $\Delta x$ is the thickness of the material, A is the area over which the heat flow is applied, $T_1$ and $T_2$ are temperatures measured on opposite sides of the material under test.

However, as discussed above, existing thermal measurement techniques are unable to measure thermal conductivity of certain components. For example, existing thermal measurement techniques are unable to adequately measure in-plane thermal conductivity of anisotropic materials. Unfortunately, such anisotropic materials are common in electronic devices. For instance, display screens, printed circuit boards (PCBs), and housings all may be anisotropic. By way of example and not limitation, anisotropic materials include composite materials comprised of multiple heterogeneous layers. In the case of an anisotropic material comprised of multiple heterogeneous layers, "in-plane" refers to a direction parallel to planes defined by the layers of the anisotropic material. In contrast, "out of plane" refers to a direction perpendicular to planes defined by the layers.

When faced with these anisotropic materials, designers cannot measure an actual in-plane thermal conductivity of the material and must instead attempt to compute an estimated in-plane thermal conductivity of the anisotropic material based on stated or known coefficients of thermal conductivity for individual constituent layers of the anisotropic materials. However, such estimates are often inaccurate due to, among other things, lack of thermal conductivity information for all layers of the anisotropic material, anisotropy of individual constituent layers, and/or inability to account for boundary conditions between the layers (e.g., contact resistances, surface finishes, etc.). This lack of accurate in-plane thermal conductivity information for anisotropic materials hampers designers' ability to design electronic devices that will perform as desired under anticipated environmental temperatures.

This disclosure describes techniques and devices to measure in-plane thermal conductivity of anisotropic materials, such as display stacks, printed circuit boards (PCBs), composite housings, and other composites having multiple heterogeneous layers of material. A thermal conductivity measurement device may apply heat to a first region of an anisotropic sample and remove heat (i.e., cool) a second region of the sample that is spaced from the first region in an in-plane direction (i.e., in a direction parallel with a surface or layers of the sample). The thermal conductivity measurement device is configured to apply heat to the sample so as to enforce heat transfer in the in-plane direction through a portion of the sample having a known geometry. The portion of the sample through which the heat transfer is defined by the shape and configuration of the thermal conductivity measurement device, without regard to the shape of the sample. Thus, the portion of the sample to be tested is of a shape that is independent of the shape of the overall sample.

In some examples, heat may be applied to the first region at opposite surfaces (e.g., top and bottom surfaces) of the sample using a pair of heating elements, and heat may be removed from the second region at opposite surfaces (e.g., top and bottom surfaces) of the sample using a pair of cooling elements. By applying heat to both sides of the sample, heat transfer from the first region to the second region may be made symmetric with respect to a mid-plane halfway between the top and bottom surfaces. In some cases, this may simplify the calculations used to determine the in-plane thermal conductivity and improve the accuracy of the in-plane thermal conductivity measurement. The thermal conductivity measurement device measures temperature at a first location at or near the first region and at a second location at or near the second region. In some examples, the first location may be adjacent the first region and the second location may be adjacent the second region. The in-plane thermal conductivity of the sample may be computed based on the temperature at the first location, the temperature at the second location, a distance from the first region to the second region, a thickness of the sample, and an amount of heat applied to the first region.

The heating and cooling elements may take different forms depending on, for example, characteristics of the sample to be tested. In some examples, the cooling elements comprise cooling rings that encircle cylindrical heating elements, such that a substantially disk shaped portion of the sample is bounded at an inner edge by a radius of the heating elements and at an outer edge by an inner radius of the cooling rings. In that case, the thermal conductivity measurement device enforces in-plane heat transfer from the cylindrically heating elements radially outward toward the cooling rings. In other examples, the heating and cooling elements may comprise elongated members (e.g., bars, channels, tubes, etc.) that are parallel to one another and spaced apart from each other a distance in an in-plane direction. A length of the elongated heating and cooling elements may be selected to be longer than a spacing between the heating and cooling elements, such that a substantially rectangular portion of the sample is bounded on its two longer sides by the heating and cooling elements and its two shorter sides are unbounded by the heating and cooling elements. In this example, the thermal conductivity measurement device enforces in-plane heat transfer linearly in a direction perpendicular from the elongated heating elements to the elongated cooling elements. As illustrated by the above examples, the direction of heat transfer is defined and controlled by the configuration (e.g., shape, size, and position) of the heating and cooling elements of the thermal conductivity measurement device. By enforcing the heat transfer in this way, variables can be eliminated and the in-plane thermal conductivity can be computed using the equations provided herein.

Techniques and devices described herein may additionally or alternatively be used to measure out of plane thermal conductivity of samples (i.e., thermal conductivity in a direction perpendicular to a surface or layers of the sample). An example configuration usable to measure out of plane thermal conductivity includes a heating element disposed on a first surface of a sample to be measured, and a cooling element disposed on a second surface opposite the first surface. A guard heat ring may be disposed around the heating element and a guard cooling ring may be disposed around the cooling element. The guard heat ring and guard cooling ring help to prevent in-plane transfer of heat in this example. That is, the guard heat ring and the guard cooling ring enforce heat transfer in the out of plane direction in this example.

The thermal conductivity measurement device of this example measures temperature at a first location at or near (e.g., adjacent) the heating element on the first side of the sample, and at a second location at or near (e.g., adjacent) the cooling element on the second side of the sample. The in-plane thermal conductivity of the sample may be computed based on the temperature at the first location, the temperature at the second location, an area of which the heat is applied, a thickness of the sample, and an amount of heat applied by the heating element.

Additional details of these and other techniques and devices are described below with reference to several examples. The following examples are merely illustrative and aspects of the various examples may be rearranged, combined, omitted, and/or otherwise modified to arrive at variations on the examples provided.

Example Thermal Conductivity Measuring System

FIG. 1 schematic view of an example thermal conductivity measuring system 100 usable for measuring in-plane and/or out of plane thermal conductivity of anisotropic materials. FIG. 1 illustrates an electronic device 102 including a display stack 104, a printed circuit board (PCB) 106, and a housing 108. All of the display stack 104, printed circuit board 106, and housing 108 in this example are anisotropic, comprised of multiple heterogeneous layers of materials. For example, the display stack 104 may include multiple different layers of glass, plastics, and adhesives. The PCB 106 may include, for example, multiple different layers of conductive and dielectric materials. The housing may include, for example, multiple different layers of metals, plastics, glass, fabrics, and adhesives. Additional details of example anisotropic materials for which thermal conductivity can be measured are provided below with reference to FIGS. 2 and 3.

Samples 110 of the display stack 104, printed circuit board 106, housing 108, may be placed in a thermal conductivity measurement device 112. In some examples, the samples 110 may constitute the whole display stack 104, printed circuit board 106, or housing 108. However, in other examples, the samples 110 may be a portion of material cut from the display stack 104, printed circuit board 106, or housing 108 material. While the samples 110 are shown in FIG. 1 as being obtained from a finished display stack 104, printed circuit board 106, and housing 108, in other examples, the samples 110 may be cut from sheets of composite material of which the display stack 104, printed circuit board 106, are to be made housing 108.

The thermal conductivity measurement device 112 of FIG. 1 is but one example, and details of several example thermal conductivity measurement devices are provided below with reference to other figures. The thermal conductivity measurement device 112 includes, among other things, a heater and a cooler. Collectively, the heater and the cooler provide a temperature differential across a portion of the sample. This temperature differential is measured by temperature sensors located proximate the heater and the cooler, respectively.

The thermal conductivity measurement device 112 is communicatively connected with a computing device 114. While the thermal conductivity measurement device 112 and computing device 114 are shown as separate devices in this figure, in other examples, the thermal conductivity measurement device 112 and computing device 114 may be integrated in a single device. By way of example and not limitation, computing device 114 may be configured as a desktop computer, a laptop computer, a tablet computer, a server, a smartphone, or the like.

In the illustrated example, the computing device 114 includes one or more processors 116 communicatively coupled to one or more sensors and/or inputs 118. The sensor(s) and/or input(s) 118 include sensors that are part of the computing device 114 as well as inputs corresponding to sensors located at the thermal conductivity measurement device 112 or other remote locations. By way of example and not limitation, sensor(s) and/or input(s) 118 may include thermocouples or other temperature sensors to measure temperatures of the sample being tested. The sensor(s) and/or input(s) 118 may additionally or alternatively include cameras, scanners, range finders, or other sensors to measure physical dimensions of the sample (e.g., thickness, length, width, etc.) and/or distances between components of the thermal conductivity measurement device (e.g., distance between heating elements and cooling elements, distance between temperature sensors and heating or cooling elements, etc.). The sensor(s) and/or input(s) 118 may additionally or alternatively include electrical sensors to measure electricity consumed by the heater (e.g., power, voltage, current, time, etc.), force sensors to measure a force applied to one or more components (e.g., force compressing heater and/or cooler to the sample).

The thermal conductivity measurement device 112 also includes a temperature controller 120 to control the heater and/or cooler of the thermal conductivity measurement device 112. The temperature controller 120 may be implemented in software and executed by the processor(s) 116, or may be implemented as a separate hardware controller. Moreover, while illustrated as part of the computing device 114, the temperature controller 120 may be part of the thermal conductivity measurement device 112. In some examples, the temperature controller 120 is configured to balance a temperature applied to opposing sides of the sample by heating elements disposed at the opposing sides of the sample. In other examples, the temperature controller 120 is configured to balance a current or power applied to heating elements located at opposing sides of the sample. Additionally or alternatively, the temperature controller 120 may be configured to control one or more pumps and/or fans of a cooling system supplying fluid to the cooler of the thermal conductivity measurement device 112.

The computing device 114 also includes a user interface 120 including one or more inputs for receiving information and commands from a user and/or one or more outputs for presenting information to user. Examples of inputs include, for example, keyboards, keypads, touchscreens, touch pads, mice, styli, buttons, knobs, microphones, scanners, cameras, and the like. Examples of outputs include, for example, display screens, speakers, projectors, printers, plotters, indicator lights, and the like. In some instances, a component may comprise both an input and an output, as in the case of a touch screen display for example.

The computing device 114 also includes communication connections 124 to allow the computing device 114 to communicate with the thermal conductivity measurement device 112 and one or more sensors or other devices. By way of example and not limitation, the communication connections 124 may include one or more radios, transceivers, modules, or other devices to enable wired and/or wireless communication (e.g., via WiFi, Bluetooth, near field communication, cellular, Ethernet, universal serial bus (USB), power line communication (PLC), or other known communication technologies.

The computing device 114 also includes memory 126 storing modules to implement various operations. In the illustrated example, the memory includes a thermal conductivity module 128, one or more other modules 130, and data 132. The data 132 may include sensor data, calculations, simulations, reports, or other data. The thermal conductivity module 128 is programmed to calculate in-plane and/or out of plane thermal conductivity of the sample based at least in part on values including measured temperatures taken at two or more locations of the sample, dimensions of the sample, and heat energy applied by the heater of the thermal conductivity measurement device 112. Various different algorithms and equations may be used to compute the thermal conductivity values, depending on the configuration of the thermal conductivity measurement device 112, the sample 110, and the type of thermal conductivity to be determined. The values upon which the thermal conductivity is calculated may be received from the sensor(s) and/or input(s) 118, temperature controller 120, user interface 122, data 132 stored in memory, or other sources. The other modules 130 may include other programs to obtain, view, model, visualize, simulate, or process thermal conductivity information.

Memory 126 is shown to include software functionality configured as one or more applications or "modules." However, the modules are intended to represent example divisions of the software for purposes of discussion, and are not intended to represent any type of requirement or required method, manner or necessary organization. Accordingly, while various "modules" are discussed, their functionality and/or similar functionality could be arranged differently (e.g., combined into a fewer number of modules, broken into a larger number of modules, etc.).

The modules may include instructions executable by the one or more processors 116 to implement the functionalities they are described as performing. The computing device 114 may additionally or alternatively include one or more hardware components (e.g., application specific integrated circuits, field programmable gate arrays, systems on a chip, and the like) to implement some or all of the functionalities the modules are described as performing.

The memory 126 described herein is an example of computer-readable media and may take the form of volatile memory, such as random access memory (RAM) and/or non-volatile memory, such as read only memory (ROM) or flash RAM. Computer-readable media includes volatile and non-volatile, removable and non-removable media implemented in any method or technology for storage of information such as computer-readable instructions, data structures, program modules, or other data for execution by one or more processors of a computing device. Examples of computer-readable media include, but are not limited to, phase change memory (PRAM), static random-access memory (SRAM), dynamic random-access memory (DRAM), other types of random access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transitory medium that can be used to store information for access by a computing device. As defined herein, computer-readable media does not include transitory media, such as modulated data signals and carrier waves.

Additional details of example thermal conductivity measurement systems and their components are further explained below with reference to the remaining figures.

Example Anisotropic Materials

Figure 2:
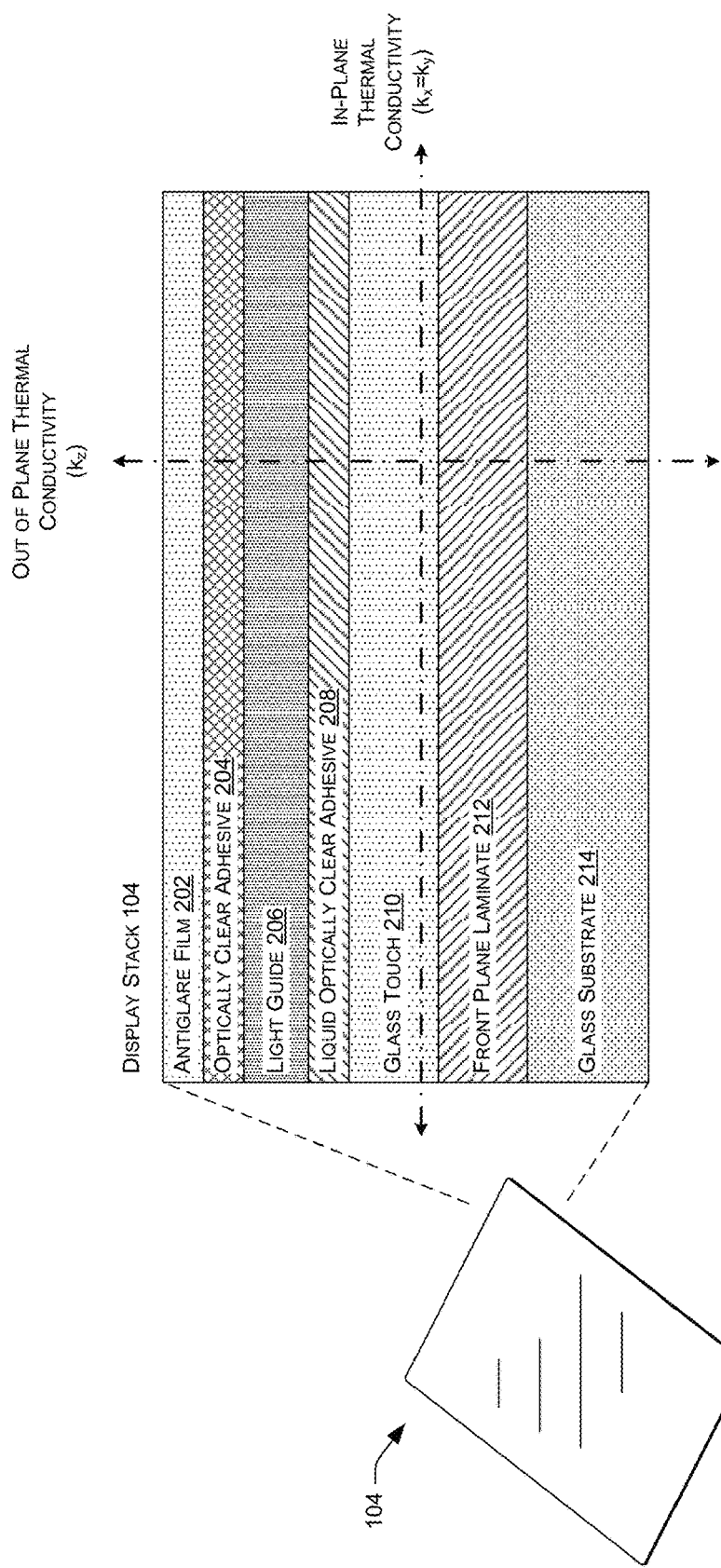
FIG. 2 is a schematic diagram of an example anisotropic sample of an electronic device display stack for which in-plane and out of plane thermal conductivity can be measured using techniques and devices described herein.
Figure 3:
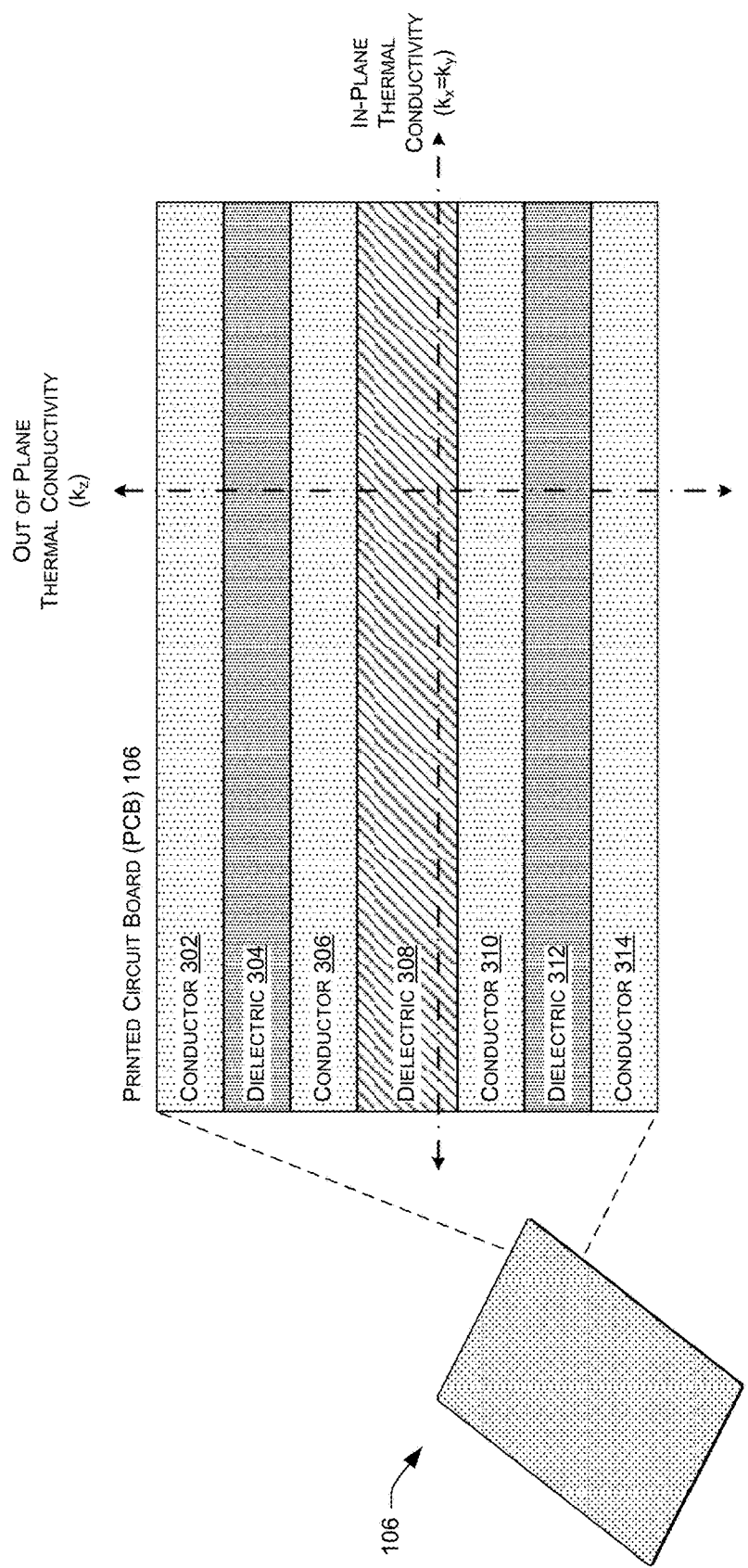
FIG. 3 is a schematic diagram of an example anisotropic sample of an electronic device printed circuit board (PCB) for which in-plane and out of plane thermal conductivity can be measured using techniques and devices described herein.

FIGS. 2 and 3 illustrate example anisotropic composite materials having multiple homogeneous layers of material. The examples shown in FIGS. 2 and 3 are substantially planar substrates. Because they are composed of multiple layers of different materials having different material properties, the in-plane conductivities ($k_x$ and $k_y$) are equal to each other, but are different than the out of plane conductivity ($k_z$) for the example anisotropic materials. As mentioned above, it may not be possible or practical to estimate a composite thermal conductivity value for such anisotropic substrates because they include materials for which thermal conductivity values are unknown or are not readily available (e.g., as in the case of thin adhesives), because individual layers themselves are anisotropic, and/or because boundary conditions between the layers (e.g., contact resistances between bonded layers, surface finishes of layers, etc.) are unknown.

FIG. 2 is a schematic diagram of an example display stack 104 of an electronic device, such as an electrophoretic or "e-ink" display. The display stack 104 includes, from top (outer surface) to bottom (closest to the interior of the electronic device), an antiglare film 202 made of polyethylene terephthalate (PET), an optically clear adhesive (OCA) 204, a light guide 206 made of acrylic, a liquid optically clear adhesive (LOCA) 208, a glass touch layer 210 made of soda lime glass, a front plane laminate (FPL) 212 (which is itself an anisotropic material), and a glass substrate 214 made of soda lime glass. This is but one example of a display stack and the techniques and devices described herein may be used to measure thermal conductivity of display stacks having different numbers of layers, different materials, and/or having substantially any thicknesses.

FIG. 3 is a schematic diagram of an example printed circuit board (PCB) 106 of an electronic device. The PCB 106 includes, from top to bottom, a first conductor layer 302, a first dielectric layer 304, a second conductor layer 306, a second dielectric layer 308, a third conductor layer 310, a third dielectric layer 312, and fourth conductor layer 314. The conductor layers may comprise copper or other conductive material. The conductor layers may all be the same or they may differ in material and/or thickness. The dielectric layers may comprise pre-preg fiberglass or other insulating material. The dielectric layers may all be the same or they may differ in material and/or thickness. For example, in the illustrated example, the second dielectric layer 308 is thicker and more rigid than the other dielectric layers. This is but one example of a PCB and the techniques and devices described herein may be used to measure thermal conductivity of PCBs having different numbers of layers, different materials, and/or having substantially any thicknesses.

Example Annular Thermal Conductivity Measurement Device

Figure 4A:
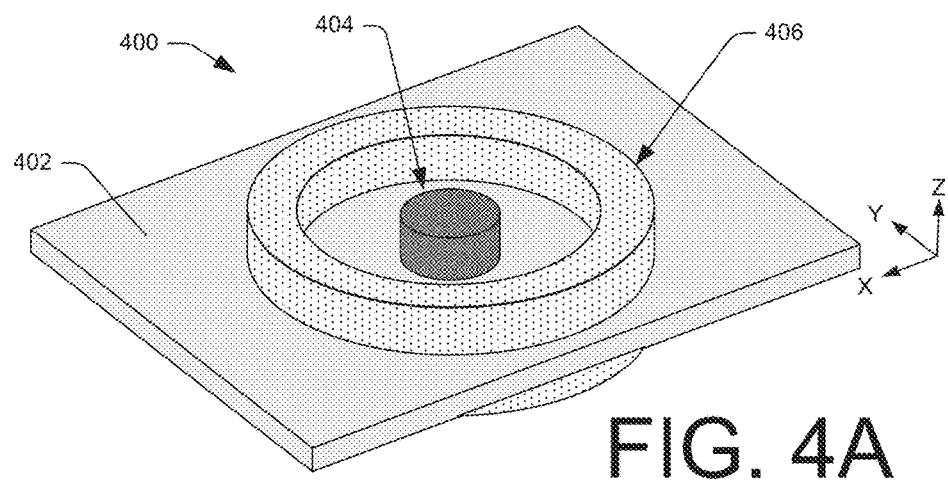
FIG. 4A is a perspective view of an example thermal conductivity measurement device usable to measure in-plane thermal conductivity of a sample. The thermal conductivity measurement device of this example includes a heater comprised of cylindrical heating elements disposed on opposite sides of the sample to be measured, and a cooler comprised of annular cooling elements or cooling rings encircling the cylindrical heating elements.
Figure 4B:
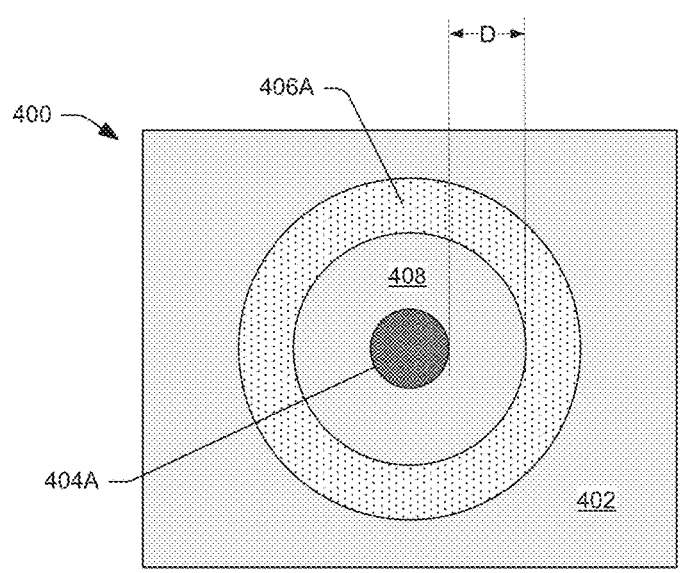
FIG. 4B, FIG. 4C, and FIG. 4D are top, side, and front views, respectively, of the example thermal conductivity measurement device of FIG. 4A.
Figure 4C:
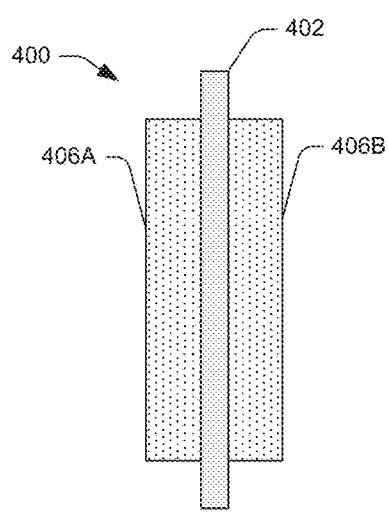
Figure 4D:
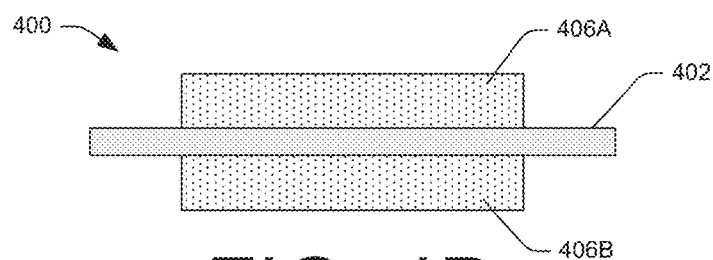

FIGS. 4A-4D illustrate an example annular thermal conductivity measurement device 400 that is capable of measuring in-plane thermal conductivity of an anisotropic substrate or other sample 402, such as a display stack, printed circuit board, composite housing, or the like. FIG. 4A is a perspective view of the example thermal conductivity measurement device 400. FIG. 4B, FIG. 4C, and FIG. 4D are top, side, and front views, respectively, of the example thermal conductivity measurement device 400.

The thermal conductivity measurement device 400 of this example includes a heater 404 comprised of cylindrical heating elements 404A and 404B (404B is not visible in this figure) disposed on opposite sides of the sample 402 to be measured, and a cooler 406 comprised of annular cooling elements 406A and 406B or cooling rings encircling the cylindrical heating elements 404A and 404B. A portion 408 of the sample 402 is interposed between and bounded radially by the heating elements 404A and 404B on an inside and the cooling elements 406A and 406B on the outside. The portion 408 of the sample 402 between the heater 404 and the cooler 406 in this example is ring shaped. However, in other examples, the shape of the bounded portion 408 may be different.

Figure 5:
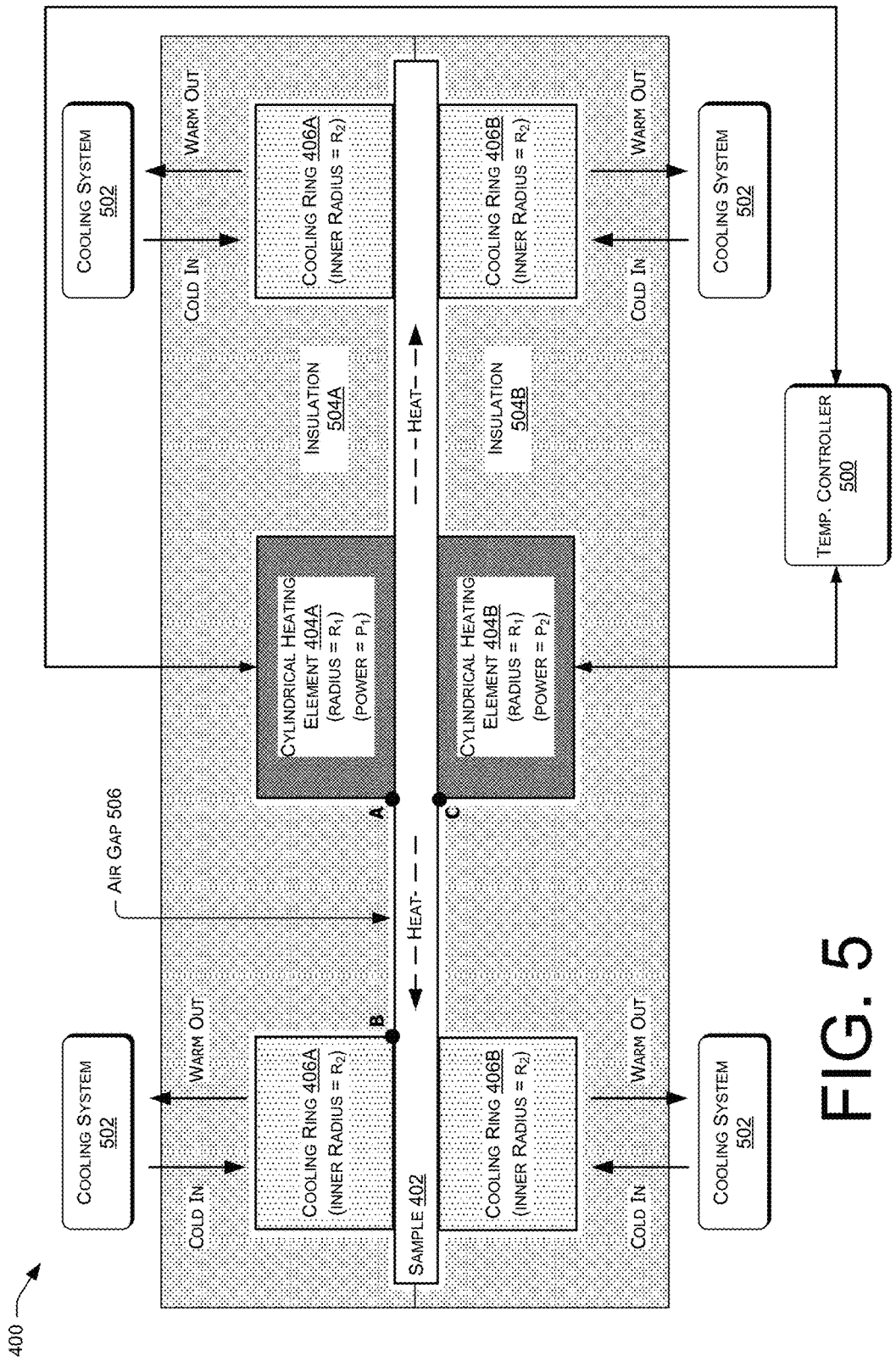
FIG. 5 is an enlarged cross-sectional view of the example thermal conductivity measurement device of FIGS. 4A-4D showing additional details.

FIG. 5 is an enlarged cross-sectional view of the example thermal conductivity measurement device 400 of FIGS. 4A-4D showing additional details. As shown in FIG. 5, the first cylindrical heading element 404A and the first cooling ring 406A are disposed on a first surface of the sample 402, and the second cylindrical heading element 404B and the second cooling ring 406B are disposed on a second surface of the sample 402. The heating elements 404A and 404B and cooling rings 406A and 406B are all axially aligned with each other about a central axis substantially perpendicular to the surface or layers of the sample 402. Thus, the sample 402 is sandwiched between the two cylindrical heating elements 404A and 404B and between the two cooling rings 406A and 406B.

The portion of the sample 402 interposed between the cylindrical heating elements 404A and 404B defines a first region at which heat is applied to the sample by the cylindrical heating elements 404A and 404B. The portion of the sample 402 interposed between the cooling rings 406A and 406B defines a second region at which heat is removed from the sample 402 by the cooling rings 406A and 406B.

A first temperature sensor A is in contact with the sample 402 proximate to the first cylindrical heating element 404A to measure a temperature of the first surface of the sample 402 proximate to the first cylindrical heating element 404A. A second temperature sensor B is in contact with the sample 402 proximate an inner edge of the first cooling ring 406A.

In the illustrated example, the first temperature sensor A and the second temperature sensor B are both disposed along a same line extending radially outward from a center of the cylindrical heating element 404A. Thus, the first temperature sensor A is positioned at a location of the first region that is closest to the second region. Likewise, the second temperature sensor is positioned at a location of the second region that is closest to the first region. Temperatures measured by the first temperature sensor A and the second temperature sensor B may be used to compute the in-plane thermal conductivity of the sample 402.

A third temperature sensor C is in contact with the sample 402 proximate to the second cylindrical heating element 404B to measure a temperature of the second surface of the sample 402. In this example, the third temperature sensor C is substantially aligned with the first temperature sensor A, but on the opposite side of the sample 402. Temperatures measured by the third temperature sensor C may be used (alone or averaged with temperatures measured by the first temperature sensor A) along with temperatures measured by the second temperature sensor B to compute the in-plane thermal conductivity of the sample 402.

In some examples, the temperature sensors A, B, and C may be adjacent to the cylindrical heating element 404A, cooling ring 406A, and cylindrical heating element 404B, respectively. As used herein, a temperature sensor is "adjacent to" an element if it is directly beside or in contact with the element or a surface or edge thereof. Positioning the temperature sensors adjacent to the respective elements may simplify the equations used to calculate the in-plane thermal conductivity. However, in other examples, the temperature sensors may be positioned at other locations of the sample (e.g., between the heating elements and the cooling elements).

In some examples, temperatures measured by the first temperature sensor A and the third temperature sensor C may be fed back to a temperature controller 500, which may use these temperature readings to equalize or balance the temperatures of the first and second cylindrical heating elements 404A and 404B to apply an equal heat to both sides of the sample 402. That is, the temperature controller 500 may regulate the power ($P_1$) or current applied by the first cylindrical heating element 404A and the power ($P_2$) or current applied by the second cylindrical heating element 404B so as to maintain a temperature measured by temperature sensor A proximate the heating element 404A substantially the same as a temperature measured by temperature sensor C proximate the heating element 404C. By applying heat to both sides of the sample and balancing the temperatures at both sides of the sample, heat transfer may be made symmetric with respect to a mid-plane halfway between the top and bottom surfaces of the sample 402. When the materials at both surfaces of the sample 402 are the same or similar, the temperature controller 500 may apply approximately the same amount of power to both heating elements 404A and 404B. However, if one surface of the sample 402 is made of a material having a significantly different thermal conductivity and/or contact resistance than the other surface, the temperature controller 500 may apply significantly different amounts of power to the first and second heating elements 404A and 404B in order to maintain the same temperature at both surfaces.

Additionally, in some examples, temperatures measured by the second temperature sensor B may be fed back to the temperature controller 500. In that case, the temperature controller 500 may control operation of one or more cooling systems 502 coupled to the cooling rings 406A and 406B to regulate a temperature of the cooling rings 406A and 406B. The cooling system(s) 502 remove heat from the cooling rings 406A and 406B to maintain the temperature of the cooling rings at a predetermined or desired temperature. In some examples, the cooling system(s) 502 may be set to remove as much heat as possible (maximum cooling), while in other examples, the cooling system(s) 502 and/or the temperature controller 500 may include or be communicatively coupled with a thermostat set to a predetermined or desired temperature for the cooling rings 406A and 406B.

The heating elements 404A and 404B in this example are 10 Watt resistive heaters, but in other configurations, heating elements with higher or lower ratings may be used. Additionally, in the setup shown in FIG. 5, heating elements are used on both sides of the sample 402, but in other examples, the setup can be reconfigured to replace on one of the heating elements with a cooling element (e.g., as in the case of the setup shown in FIG. 11 to measure out of plane thermal conductivity).

In some examples, a thermal interface material or thermal grease may be disposed between the surfaces of the sample 402, the heating elements 404A and 404B, and/or the cooling elements 406A and 406B, to improve the thermal bond.

In some examples, insulation is disposed between the cylindrical heating elements 404A and 404B and the cooling rings 406A and 406B to insulate against radiant heat transfer between the cylindrical heating elements 404A and 404B and the cooling rings 406A and 406B. Insulation may additionally or alternatively be provided around all exposed surfaces of the heating elements 404A and 404B, the cooling rings 406A and 406B, and/or sample 402, to prevent heat transfer to and/or from the sample 402 from the ambient environment. In the example of FIG. 5, a two-piece or clamshell arrangement is used in which a first piece of insulation 504A is disposed on the first side of the sample 402 and a second piece of insulation 504B is disposed on the second side of the sample 402. By way of example and not limitation, the insulation may comprise fiberglass insulation, polystyrene, expanded foam plastic, or any other thermally insulating material. In addition, in some examples, a small air gap 506 (e.g., 1-5 millimeters) may be maintained between the insulation 504A and 504B and the sample 402, the heating elements 404A and 404B, and/or the cooling rings 406A and 406B. The air gap 506 provides further thermal insulation and helps to prevent heat transfer due to conduction.

Figure 6:
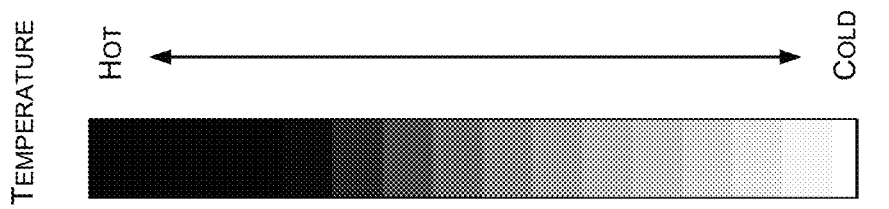
FIG. 6 is a schematic diagram representing a ring shaped portion of the sample shown in FIGS. 4A-4D that is interposed between a radius $R_1$ of the cylindrical heating elements and an inner radius $R_2$ of the cooling rings of the thermal conductivity measurement device of FIGS. 4A-4D.
Figure 6:
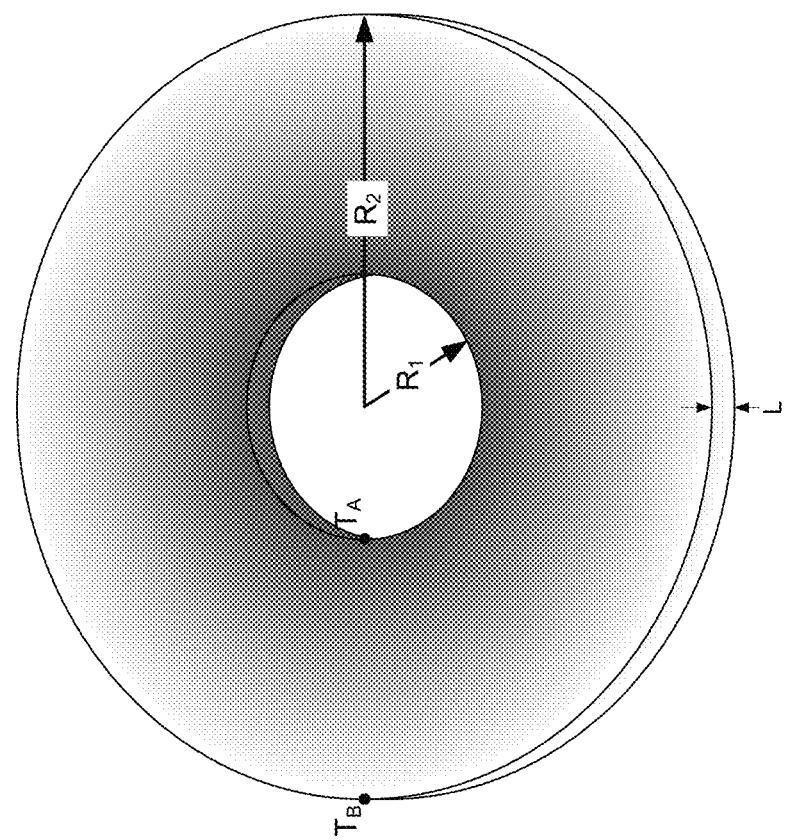

FIG. 6 is a schematic diagram representing the bounded portion 408 of the sample 402 between the cylindrical heating elements 404A and 404B and the cooling rings 406A and 406B. The portion 408 of the sample has a ring or washer shape, having an inner perimeter equal to the radius $R_1$ of the cylindrical heating elements 404A and 404B and an outer perimeter equal to the inner radius $R_2$ of the cooling rings 406A and 406B, and has a thickness L equal to a thickness of the sample 402.

FIG. 6 illustrates a thermal simulation of the bounded portion 408 of the sample 402 under test. As shown, heat applied by the heating elements 404A and 404B is transferred to the inner perimeter of the bounded portion 408 and travels outward toward the outer perimeter. Thus, the bounded portion 408 is hottest, having a temperature $T_A$ measured by the first temperature sensor A, closest to the inner perimeter and gradually cools to a temperature $T_B$ measured by the second temperature sensor B at the outer perimeter.

With this geometry, in one example, the in-plane thermal conductivity ($k_{xy}$) of the bounded portion 408 of the sample can be calculated according to the following equation:

$$k_{xy} = \ln(R_2/R_1)(P_1+P_2) \div 2\pi L(T_A-T_B) \quad (2)$$

where $P_1$ is the power consumed by the first heating element 404A, $P_2$ is the power consumed by the second heating element 404B, L is the thickness of the sample and is smaller than $R_1$, $T_A$ is the temperature at the inner perimeter measured by the first temperature sensor A, $T_B$ is the temperature at the outer perimeter measured by the second temperature sensor B, $R_1$ is the inner radius of the bounded portion 408 and $R_2$ is the outer radius of the bounded portion 408.

Example Elongated Thermal Conductivity Measurement Device

Figure 7A:
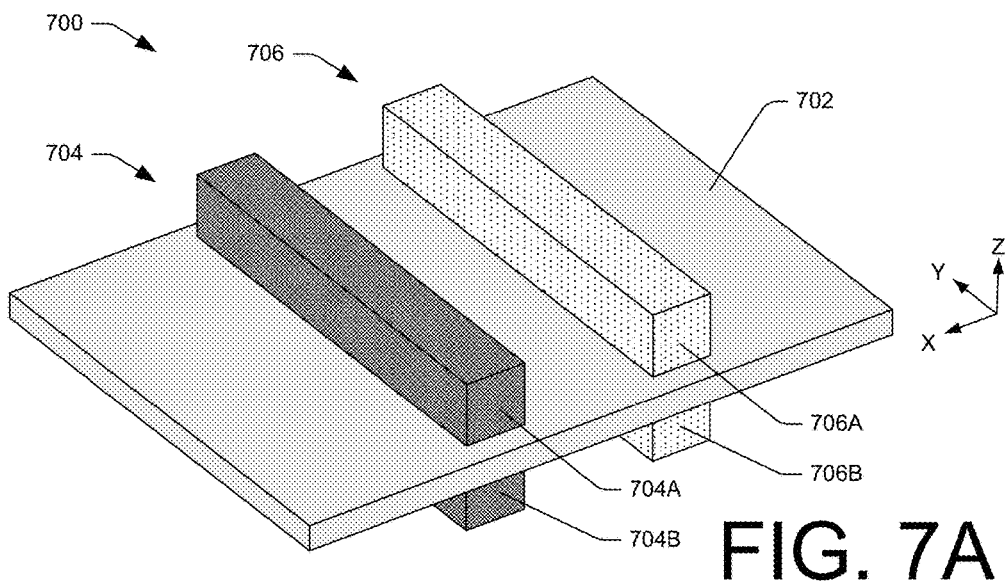
FIG. 7A is a perspective view of another example thermal conductivity measurement device usable to measure in-plane thermal conductivity of a sample. The thermal conductivity measurement device of this example includes a heater comprised of elongated heating elements disposed on opposite sides of a sample to be measured, and a cooler comprised of elongated cooling elements spaced from the elongated heating elements.
Figure 7B:
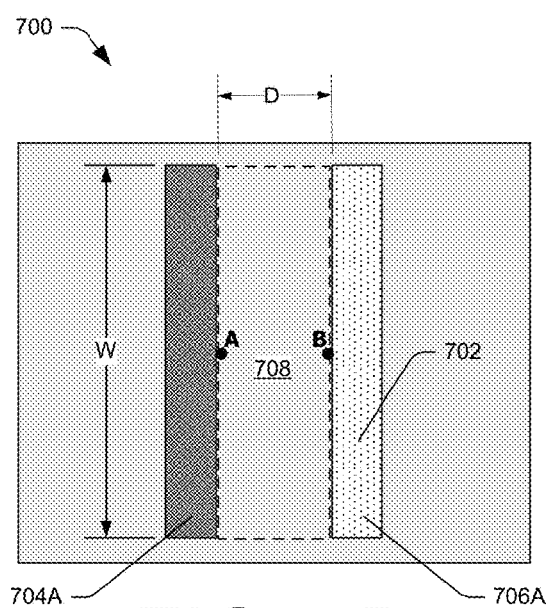
FIG. 7B, FIG. 7C, and FIG. 7D are top, side, and front views, respectively, of the example thermal conductivity measurement device of FIG. 7A.
Figure 7C:
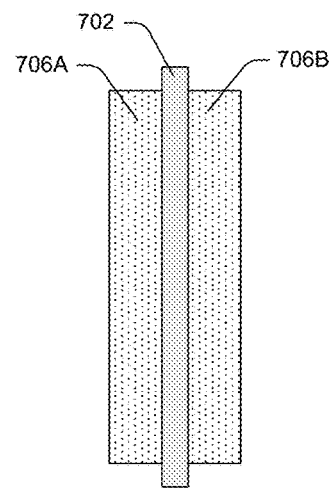
Figure 7D:
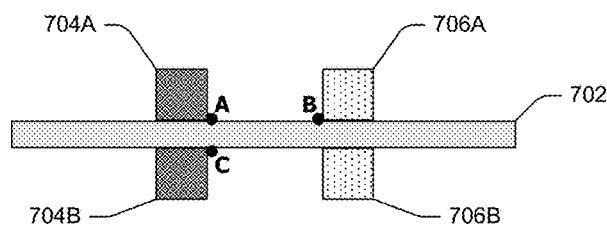

FIG. 7A is a perspective view of an example elongated thermal conductivity measurement device 700 usable to measure in-plane thermal conductivity of a sample 702. FIG. 7B, FIG. 7C, and FIG. 7D are top, side, and front views, respectively, of the example thermal conductivity measurement device of FIG. 7A.

The thermal conductivity measurement device 700 of this example includes a heater 704 comprised of elongated heating elements 704A and 704B disposed on opposite sides of the sample 702 to be measured, and a cooler 706 comprised of elongated cooling elements 706A and 706B spaced from the elongated heating elements 704A and 704B by a distance D. First, second, and third temperature sensors may be located at locations A, B, and C.

A rectangular portion 708 of the sample 702 is interposed between and partially bounded on one long edge by the heating elements 704A and 704B on the other long edge by the cooling elements 706A and 706B. The rectangular portion 708 is shown by dashed lines in FIG. 7B. The fact that the short edges of the rectangular portion 708 are not bordered by the heating and cooling elements does not impact the thermal conductivity measurements with this setup as long as the length W of the elongated heating elements 704A and 704B and cooling elements 706A and 706B exceeds the distance D between the heating elements 704A and 704B and cooling elements 706A and 706B, and as long as the temperature sensors are placed at or near a middle of the elongated heating elements 704A and 704B and cooling elements 706A and 706B. The portion 708 of the sample 702 between the heater 704 and the cooler 706 in this example is substantially rectangular. However, in other examples, the shape of the bounded portion 708 may be different.

Figure 8:
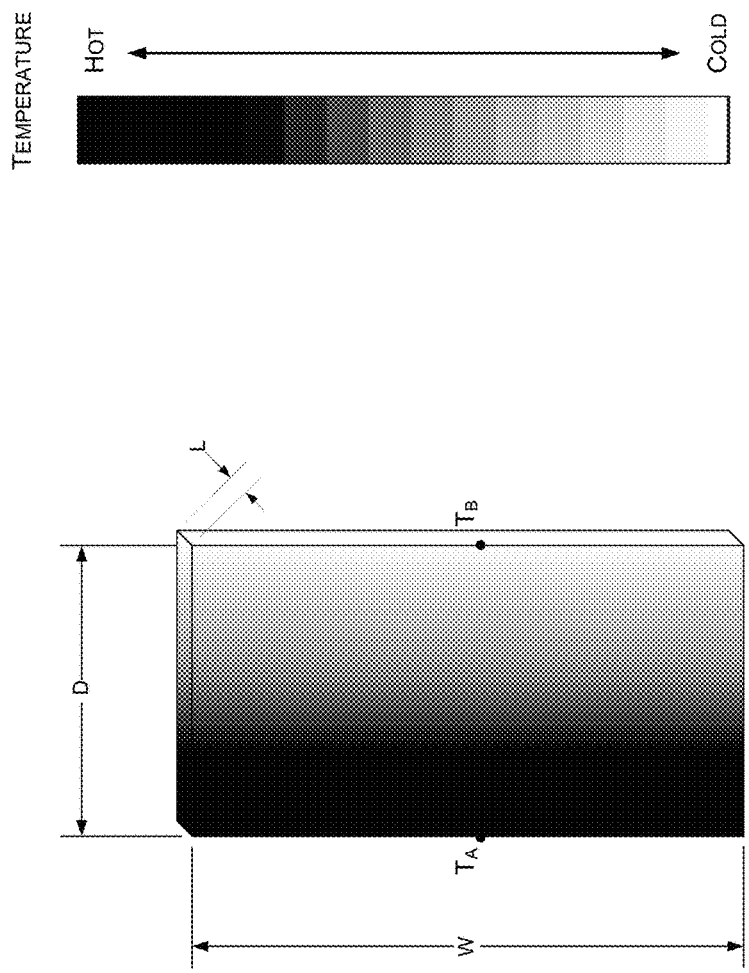
FIG. 8 is a schematic diagram representing a rectangular portion of the sample shown in FIGS. 7A-7D that is interposed between the elongated heating elements and the elongated cooling elements of the thermal conductivity measurement device of FIGS. 7A-7D.

FIG. 8 illustrates a thermal simulation of the rectangular portion 708 of the sample 702 shown in FIGS. 7A-7D that is interposed between the elongated heating elements 704A and 704B and elongated cooling elements 706A and 706B of the thermal conductivity measurement device 700. As shown, heat applied by the elongated heating elements 704A and 704B is transferred to one long edge of the rectangular portion 708 and travels outward toward the other long edge of the rectangular portion 708. Thus, the rectangular portion 708 is hottest along the edge closest to the elongated heating elements 704A and 704B, having a temperature $T_A$ measured by the first temperature sensor A, and gradually cools to a temperature $T_B$ measured by the second temperature sensor B at the edge closest to the elongated cooling elements 706A and 706B.

In this setup however, only a portion of the heat applied by the elongated heating elements 704A and 704B is transferred to the rectangular portion 708. Specifically, once heat is transferred to the sample by the elongated heating elements 704A and 704B it will radiate out into the sample in all directions. However, for this measurement, we are only concerned with measuring the portion of the heat that is transferred into the rectangular portion 708 of the sample 702, which can be expressed by the following equation:

$$Q_t = (P_1+P_2)(W/C) \quad (3)$$

where $Q_t$ is the amount of heat transferred to the rectangular portion 708 of the sample 702, $P_1+P_2$ is the total amount of heat transferred to the sample 702 by the heating elements, W is the length of the elongated heating elements, and C is the circumference C of the area over which the heating elements contact the sample 702. In other words, the ratio of the heat energy that is transmitted to the rectangular portion 708 relative to the total heat energy transmitted to the sample 702 is approximately equal to the ratio of the length W of the elongated heating elements to the circumference C of elongated heating elements. Once the heat energy transmitted to the rectangular portion 708 is determined, the in-plane thermal conductivity $k_{xy}$ of the sample can be calculated according to the following equation:

$$k_{xy} = (Q_t D) \div WL(T_A-T_B) \quad (4)$$

where Qt is the amount of heat transferred to the rectangular portion 708 of the sample 702, D is the distance between the elongated heating elements and the elongated cooling elements, W is the length of the elongated heating elements, L is the thickness of the sample 702, $T_A$ is the temperature measured by the first temperature sensor A, and $T_B$ is the temperature measured by the second temperature sensor B.

The foregoing are two examples of devices to measure in-plane thermal conductivity. However, other configurations are also possible.

Example Cooling Systems

Figure 9:
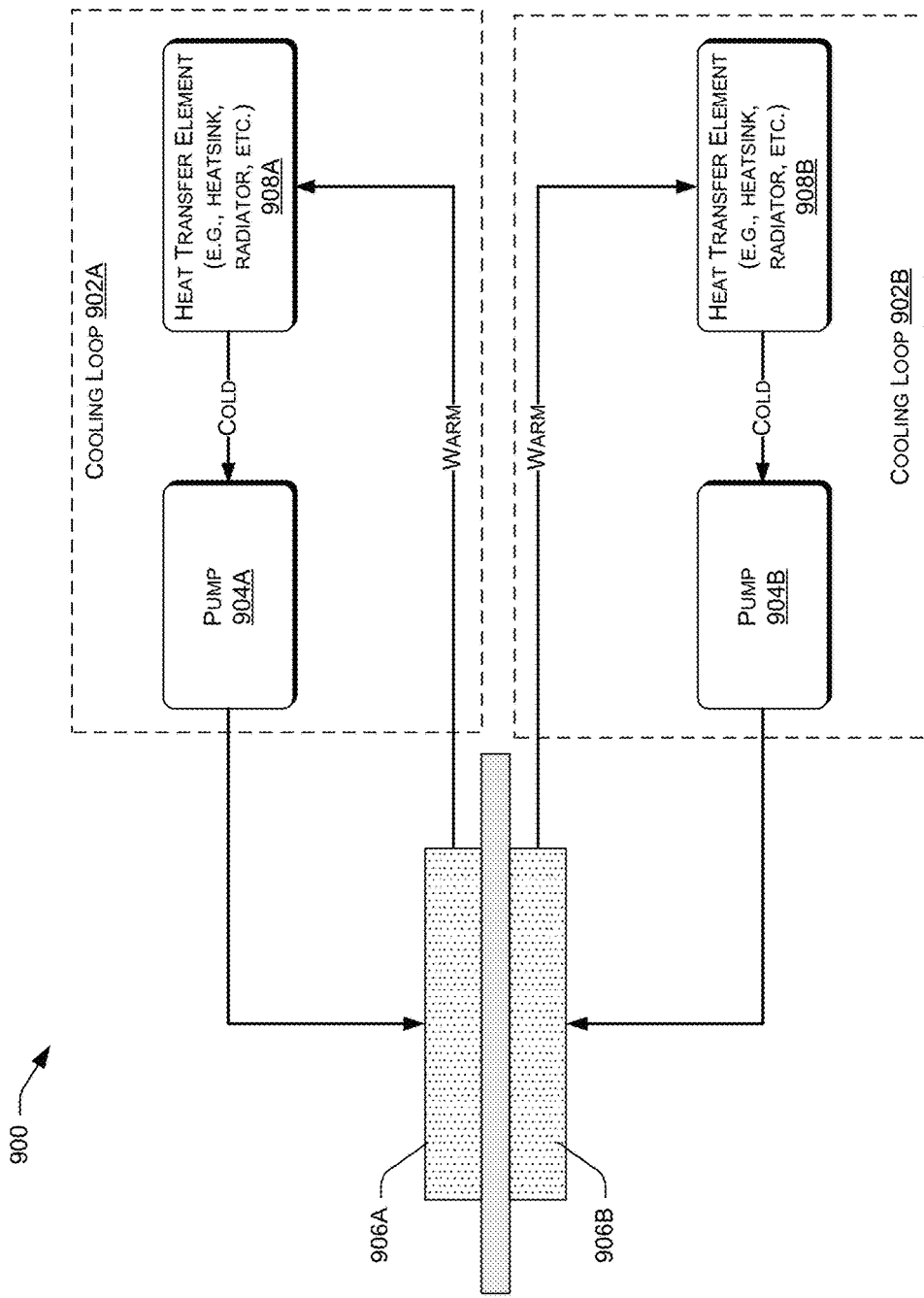
FIG. 9 is a schematic diagram of an example cooling system usable with thermal conductivity measurement devices.

FIG. 9 is a schematic diagram of a first example cooling system 900 usable with thermal conductivity measurement devices, such as those described with reference to FIGS. 4A-4D, 5, and 7A-7D. For example, the cooling system 900 may be used as the cooling system 502 shown in FIG. 5. In the example of FIG. 9, the cooling system 900 has two isolated cooling loops 902A and 902B, each of which may be fluidly connected to a respective cooling element (e.g., cooling ring, elongated cooling element, or other cooling element). Specifically, in the illustrated example, a pump 904A in first cooling loop 902A pumps cool fluid (e.g., water, refrigerant, etc.) into a first cooling element 906A (e.g., cooling ring, elongated cooling element, etc.) where it removes heat from a sample of material under test. As heat is removed from the sample, it warms the fluid in the cooling element 906A. The warm fluid flows out of the cooling element 906A and into a heat transfer element 908A, which removes heat from the fluid before the cooled fluid is pumped back to the cooling element 906A. By way of example and not limitation, the heat transfer element 908A may comprise a finned heatsink, a radiator, or the like. The heat transfer element 908A may further include a fan to enhance the heat transfer rate and/or a thermostat to regulate a temperature to which the fluid is cooled.

The second cooling loop 902B is similarly configured to the first loop, including a pump 904B to pump cooling fluid to a second cooling element 906B and a heat transfer element 908B to remove heat from the fluid before returning it cooled to the cooling element 908B. In this example, the cooling loops 902A and 902B are isolated. With this two-loop system, the temperature of the fluid in each cooling loop may be maintained at a same temperature or at different temperatures. This may facilitate different and/or more customized testing scenarios.

Figure 10:
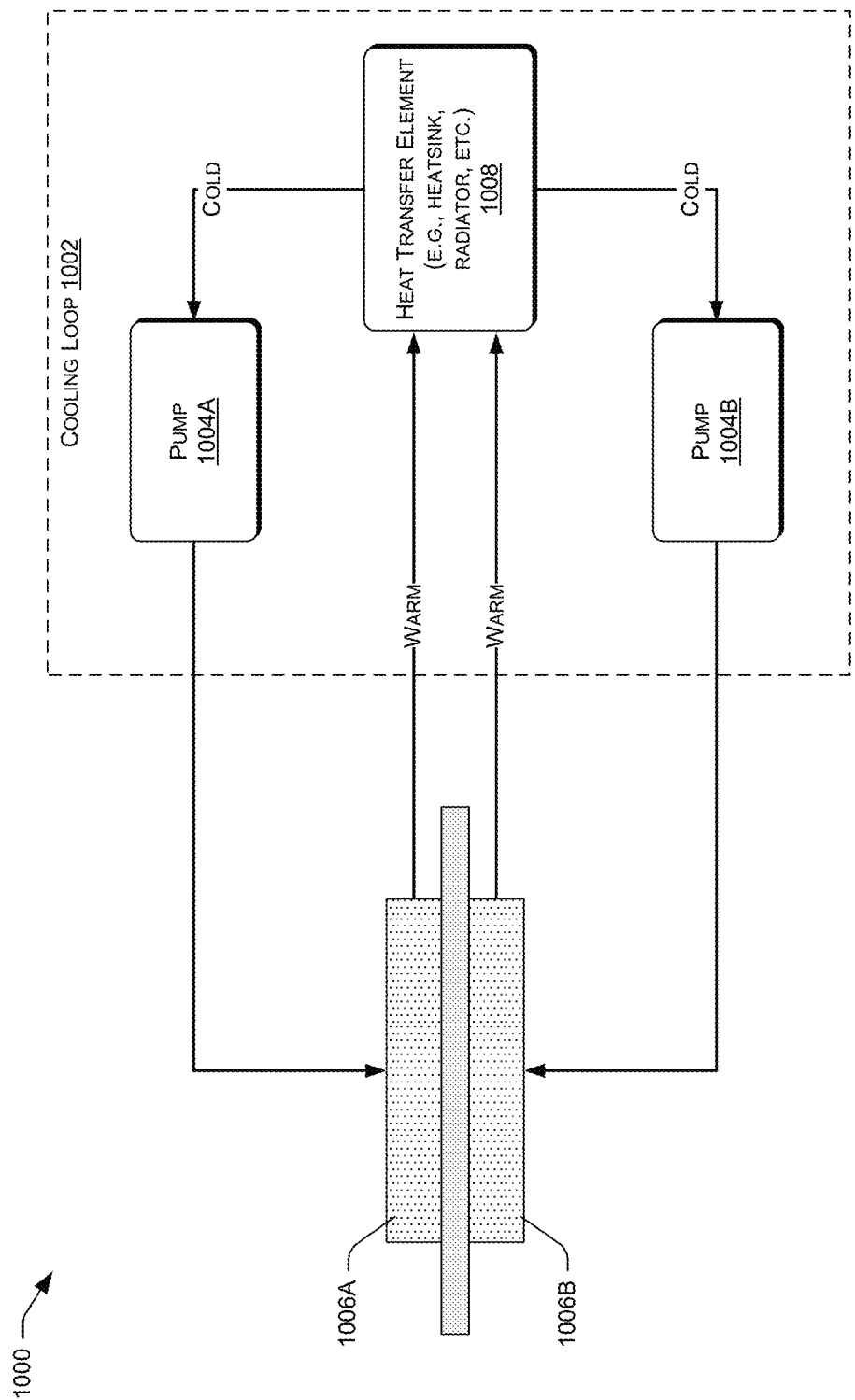
FIG. 10 is a schematic diagram of another example cooling system usable with thermal conductivity measurement devices.

FIG. 10 is a schematic diagram of another example cooling system 1000 usable with thermal conductivity measurement devices, such as those described with reference to FIGS. 4A-4D, 5, and 7A-7D. For example, the cooling system 1000 may be used as the cooling system 502 shown in FIG. 5. In the example of FIG. 10, the cooling system 1000 has a single cooling loop 902, which may be fluidly connected to both cooling elements (e.g., cooling rings, elongated cooling elements, or other cooling elements). Specifically, in the illustrated example, a first pump 1004A pumps cool fluid (e.g., water, refrigerant, etc.) into a first cooling element 1006A (e.g., cooling ring, elongated cooling element, etc.) where it removes heat from a sample of material under test. As heat is removed from the sample, it warms the fluid in the cooling element 1006A. The warm fluid flows out of the cooling element 1006A and into a heat transfer element 1008, which removes heat from the fluid before the cooled fluid is pumped back to the cooling element 1006A. By way of example and not limitation, the heat transfer element 1008 may comprise a finned heatsink, a radiator, or the like. The heat transfer element 1008 may further include a fan to enhance the heat transfer rate and/or a thermostat to regulate a temperature to which the fluid is cooled.

In this example, the heat transfer element 1008 also supplies cooled fluid to a second pump 1004B which pumps the cooling fluid to a second cooling element 1006B. Thus, in this example, the cooling fluid is supplied to both cooling elements 1006A and 1006B from the same heat transfer element 1008. This single loop system ensures that the fluid is supplied to both cooling elements 1006A and 1006B at a same temperature. This may provide for a simpler system and may eliminate potential inaccuracies due to differences in the temperature of cooling fluid supplied to each of the cooling elements 1006A and 1006B.

Example Out of Plane Thermal Conductivity Measurement Device

Figure 11:
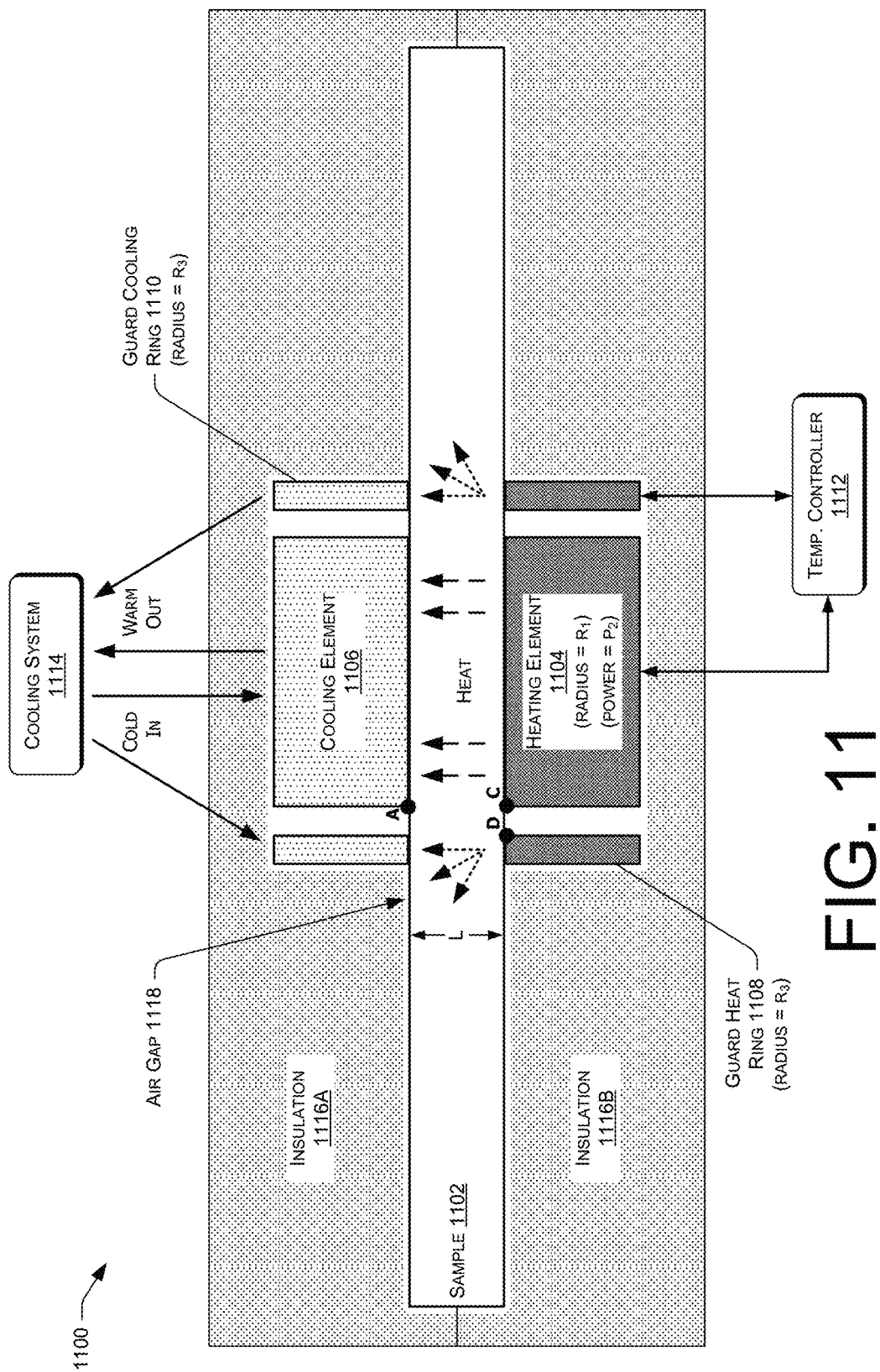
FIG. 11 is a cross-sectional view of an example thermal conductivity measurement device usable to measure out of plane thermal conductivity of a sample.

FIG. 11 is a cross-sectional view of an example thermal conductivity measurement device 1100 usable to measure out of plane thermal conductivity of a sample 1102. The thermal conductivity measurement device 1100 includes a heating element 1104 disposed on one side of the sample 1102, and a cooling element 1106 disposed on the opposite side of the sample 1102. The heating element 1104 and the cooling element 1106 may by cylindrical and may be axially aligned with one another. In some examples, a guard heat ring 1108 and a guard cooling ring 1110 may be disposed around the heating element 1104 and cooling element 1106, respectively, to minimize or eliminate in-plane heat flow in the portion of the sample that is being measured.

In this example, heat applied by the heating element 1104 passes through the thickness L of the sample 1102 toward the cooling element 1106. A temperature sensor A may be in contact with the sample 1102 proximate to the cooling element 1106 to measure a temperature of a surface of the sample 1102 that is in contact with the cooling element 1106. A temperature sensor C may be in contact with the sample 1102 proximate to the heating element 1104 to measure a temperature of a surface of the sample 1102 that is in contact with the heating element 1104. A temperature sensor D may be in contact with the sample 1102 proximate to the guard heat ring 1108 to measure a temperature of a surface of the sample 1102 that is in contact with the guard heat ring 1108. In some examples, the temperature sensors A, C, and D may be adjacent to the cooling element 1106, heating element 1104, and guard heat ring 1108, respectively. As used herein, a temperature sensor is "adjacent to" an element if it is directly beside or in contact with the element or a surface or edge thereof.

The heating element 1104 is coupled to a temperature controller 1112, which may control a temperature of the heating element 1104 or a power applied to the heating element 1104. In some examples, the guard heat ring 1108 may also be coupled to the temperature controller 1112. In that case, the temperature controller 1112 may regulate the heat applied by the heating element 1104 and the guard heat ring 1108 to maintain a temperature $T_C$ measured by temperature sensor C proximate the guard heat ring 1108 substantially the same as a temperature $T_D$ measured by temperature sensor D proximate the heating element 1104.

By including the guard heat ring 1108 and guard cooling ring 1110, the area of the sample 1102 over which heat transfer is imparted extends to the radius $R_3$ of the guard heat ring 1108 and the guard cooling ring 1110. However, the heat flow can be measured for a smaller portion of the sample 1102 (i.e., the area defined by the radius $R_1$ of the heating element 1104) using temperature sensors A and C. As shown by the dotted arrows in FIG. 11, heat transfer at an outer perimeter of the guard heat ring 1108 has both in-plane and out of plane components. However, by equalizing the temperatures $T_C$ and $T_D$ and expanding the area over which heat is imparted, the heat transfer in the portion of the sample being measured (shown by the dashed arrows in FIG. 11) is substantially only in the out of plane direction. Thus, the guard rings substantially reduce or eliminate in-plane heat flow in the portion of the sample being measured.

Alternatively, in other examples, the guard heat ring 1108 may be omitted and the temperature sensor C may be interposed between the heating element 1104 and the sample 1102 at a location spaced a distance inside the perimeter of the heating element 1104. For instance, the temperature sensor C may be embedded in the surface of the heating element 1104 that contacts the sample 1102. Similarly, the guard heat cooling 1110 may be omitted and the temperature sensor A may be interposed between the cooling element 1106 and the sample 1102 at a location spaced a distance inside the perimeter of the cooling element 1106. This alternative arrangement may also be effective to reduce or eliminate in-plane heat flow at the locations at which the temperature is being measured.

As shown in FIG. 11, a cooling system 1114 is coupled to the cooling element 1106 and the guard cooling ring 1110 to remove heat from the sample 1102. Additional details of example cooling systems are provided with reference to FIG. 13.

Also, like the example of FIG. 5, the thermal conductivity measurement device 1100 may include insulation 1116A and 1116B and an air gap 1118 to insulate the heating element 1104, cooling element 1106, and/or sample 1102 against heat loss to the environment.

While FIG. 11 is described as another example, it may also be thought of as a modified setup of the example shown in FIG. 5, in which one of the cylindrical heating elements is replaced with a cylindrical cooling element, the two cooling rings are omitted, and guard heat ring 1108 and guard cooling ring 1110 are added.

Figure 12:
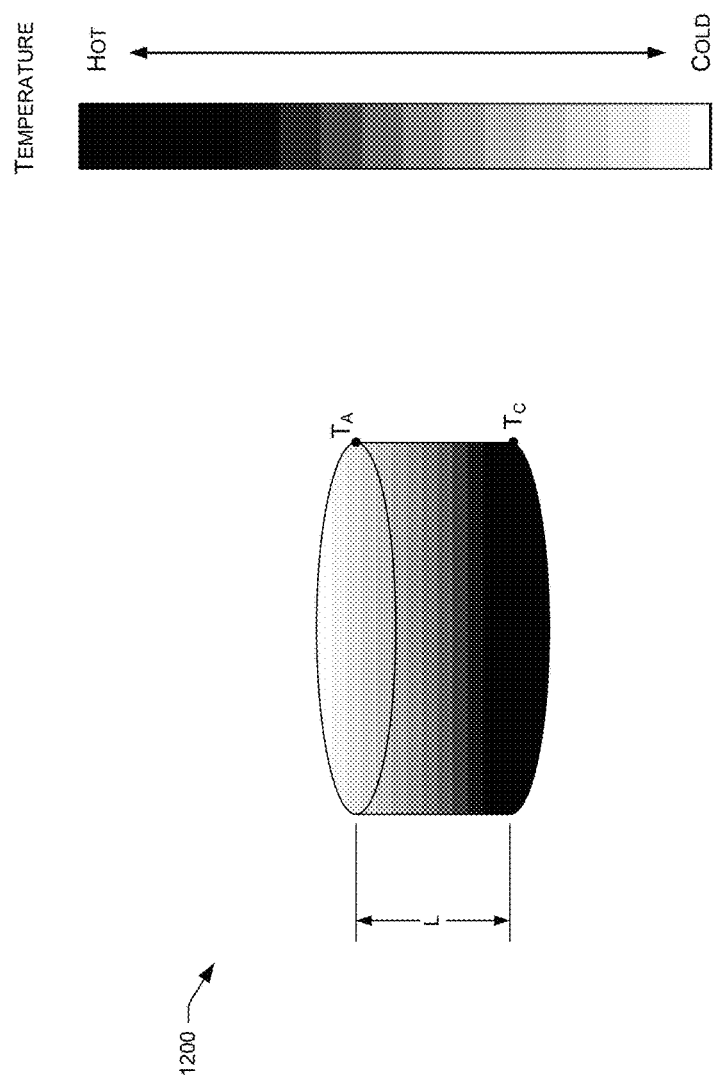
FIG. 12 is a schematic diagram representing a rectangular portion of the sample shown in FIG. 11 that is interposed between the heating and cooling elements of the thermal conductivity measurement device of FIG. 11.

FIG. 12 illustrates a thermal simulation of a portion 1200 of the sample 1102 sandwiched between the heating element 1104 and cooling element 1106 of the thermal conductivity measurement device 1100. As shown, heat applied by the heating element 1104 flows through the thickness L of the portion 1200 and travels toward the cooling element 1106. Thus, the portion 1200 is hottest along the surface closest to the heating element 1104, having a temperature $T_C$ measured by the temperature sensor C, and gradually cools to a temperature $T_A$ measured by the temperature sensor A at the surface closest to the cooling element 1106.

In this setup, the out of plane thermal conductivity $k_z$ of the sample 1102 can be found using the following equation:

$$k_z = P_2 L \div \pi (R_1)^2 (T_C - T_A) \quad (5)$$

where $P_2$ is the power of the cylindrical heater 1104, L is the thickness of the sample 1102, $R_1$ is the radius of the cylindrical heating element 1104, $T_C$ is the temperature measured by the first temperature sensor C proximate the heating element 1104, and $T_A$ is the temperature measured by the second temperature sensor A proximate the cooling element 1106.

Figure 13:
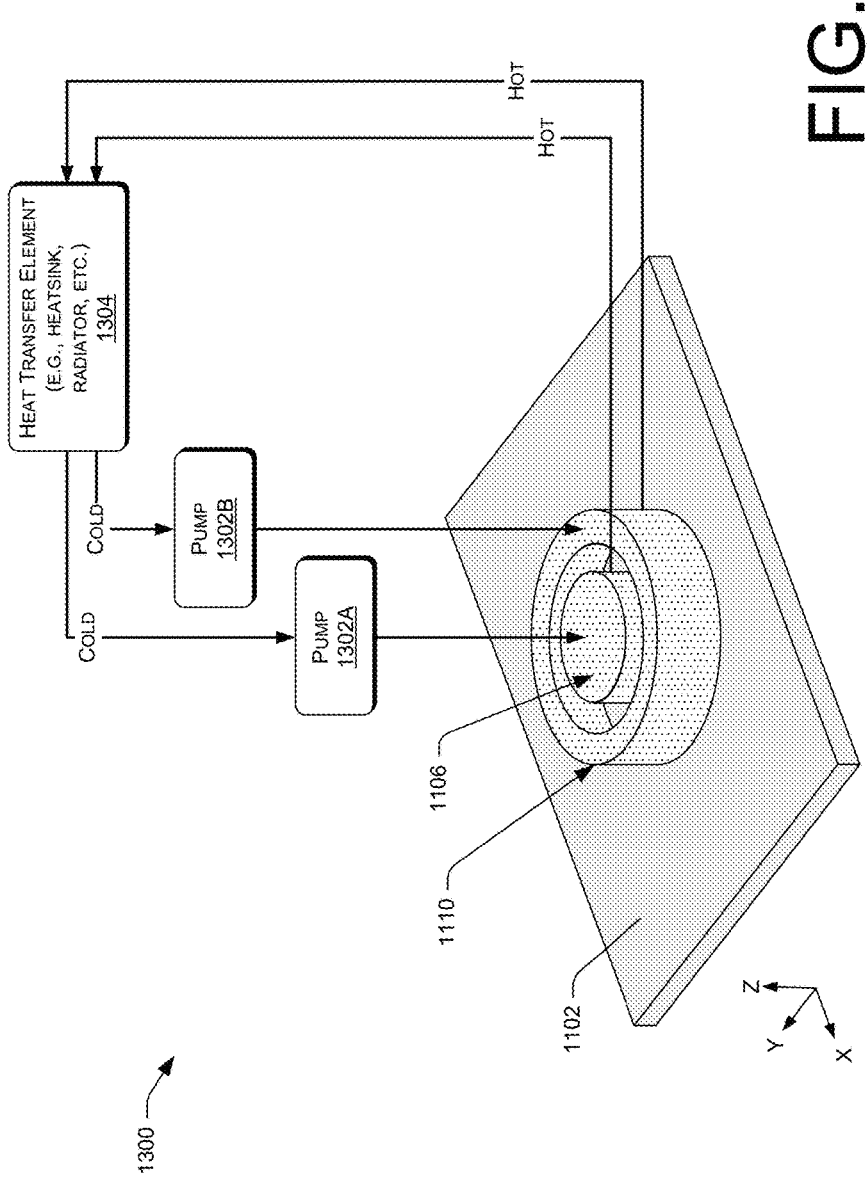
FIG. 13 is a schematic diagram of an example cooling system usable with the thermal conductivity measurement device of FIG. 11.

FIG. 13 is an example cooling system 1300 usable with the thermal conductivity measurement device 1100. The cooling system 1300 is fluidly connected to the cooling element 1106 and the guard cooling ring 1110. The cooling system 1300 includes a pump 1302A that pumps cool fluid (e.g., water, refrigerant, etc.) into the cooling element 1106 and a pump 1302B that pumps cool fluid into the guard cooling ring 1110, where it removes heat from a sample of material under test 1102. As heat is removed from the sample 1102, it warms the fluid in the cooling element 1106 and the guard cooling ring 1110. The warm fluid flows out of the cooling element 1106 and the guard cooling ring 1110 and into a heat transfer element 1304, which removes heat from the fluid before the cooled fluid is pumped back to the cooling element 1106 and the guard cooling ring 1110. By way of example and not limitation, the heat transfer element 1304 may comprise a finned heatsink, a radiator, or the like. The heat transfer element 1304 may further include a fan to enhance the heat transfer rate and/or a thermostat to regulate a temperature to which the fluid is cooled.

Example Frame

Figure 14:
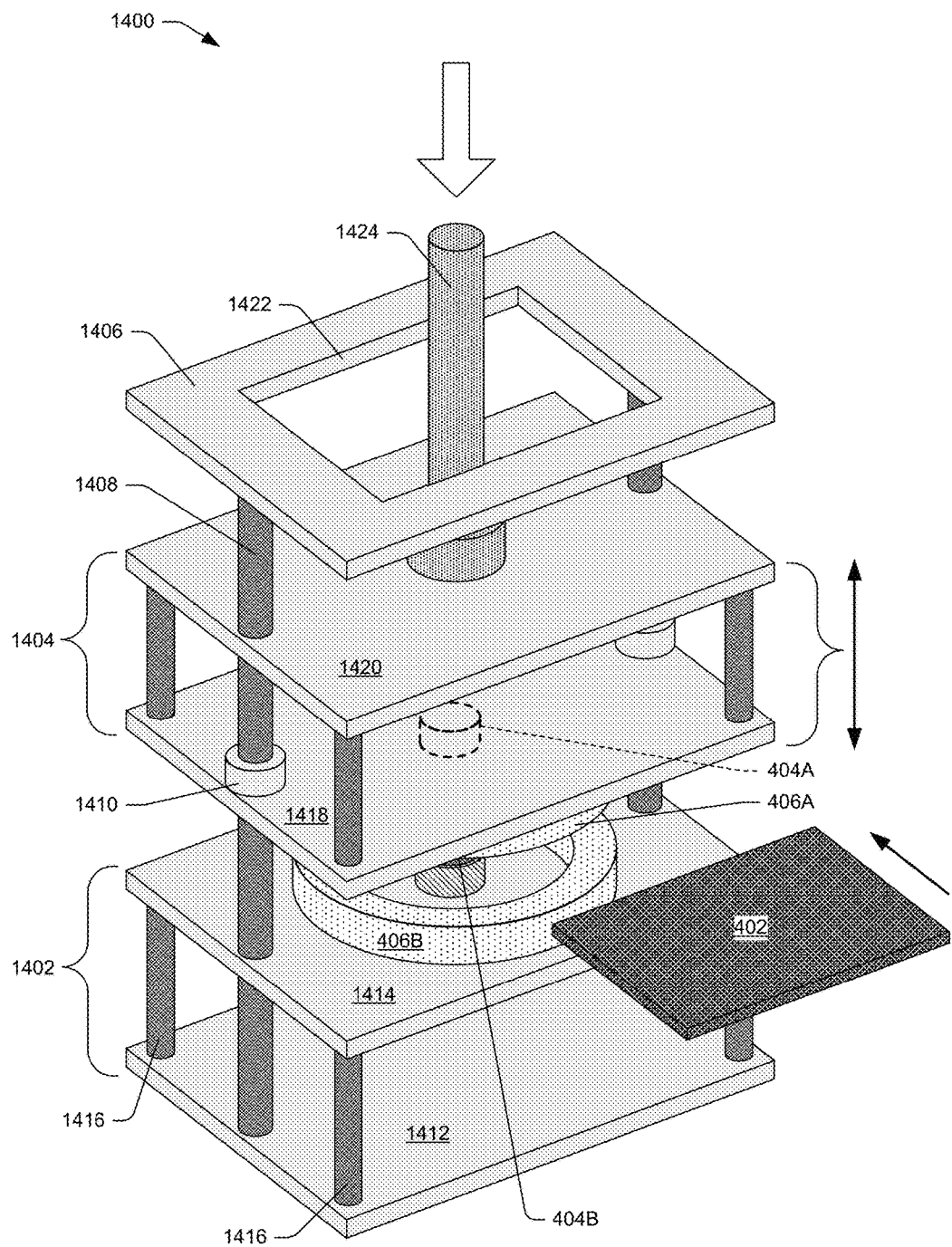
FIG. 14 is a perspective view of an example frame to support a thermal conductivity measurement device.

FIG. 14 is a perspective view of an example frame 1400 to support a thermal conductivity measurement device, such as thermal conductivity measurement devices 400 and 700. The frame 1400 is illustrated with the thermal conductivity measurement device 400 installed therein for ease of explanation. The frame 1400 includes a foot assembly 1402, a movable middle assembly 1404, and a fixed cap 1406. The foot assembly 1402 and the cap 1406 are coupled together by a pair of support columns 1408 which extend substantially the height of the frame 1400. The movable assembly 1404 is disposed between the foot assembly 1402 and the cap 1406 and is slidably coupled to the support columns 1408 by bearings 1410. In some examples, the movable middle assembly 1404 may be movable under power of an electric motor (not shown) and/or may be spring loaded into a raised or lowered position.

The foot assembly 1402 supports the frame 1400 on the floor or other support surface, and is comprised of a base 1412 and a top 1414, which are spaced apart from each other and coupled together by four corner pillars 1416. The top 1414 of the foot assembly 1402 supports a cooling element (e.g., the second cooling ring 406B) and a heating element (e.g., second cylindrical heating element 404BB).

The movable middle assembly 1404 is comprised of a bottom platform 1418 and a top platform 1420, which are spaced apart from each other and coupled together by four corner pillars 1416. The movable middle assembly 1404 has mounted to it a cooling element (e.g., the first cooling ring 406A) and a heating element (e.g., first cylindrical heating element 404A). A sample of material to be measured (e.g., sample 402) may be inserted in the frame between the foot assembly 1402 and the movable middle assembly 1404. The movable middle assembly 1404 may then be lowered into place, sandwiching the sample 402 between the upper heating and cooling elements and the lower heating and cooling elements.

The top 1406 includes an opening 1422, through which downward pressure can be applied to the top platform 1420 by a press 1424. The downward pressure compresses the sample 402 between the respective heating and cooling elements to ensure even contact is made between the heating and cooling elements and the sample.

The press 1424 may, for example, comprise a jack (e.g., a hydraulic jack, screw jack, scissor jack, etc.) or clamp that presses against the top 1406 or other elevated support structure, a heavy weight that is placed on the top platform 1420 through the opening 1422, or the like.

The frame 1400 is usable with any of the thermal conductivity measurement devices and systems described herein.

Example Thermal Conductivity Measurement Processes

Figure 15:
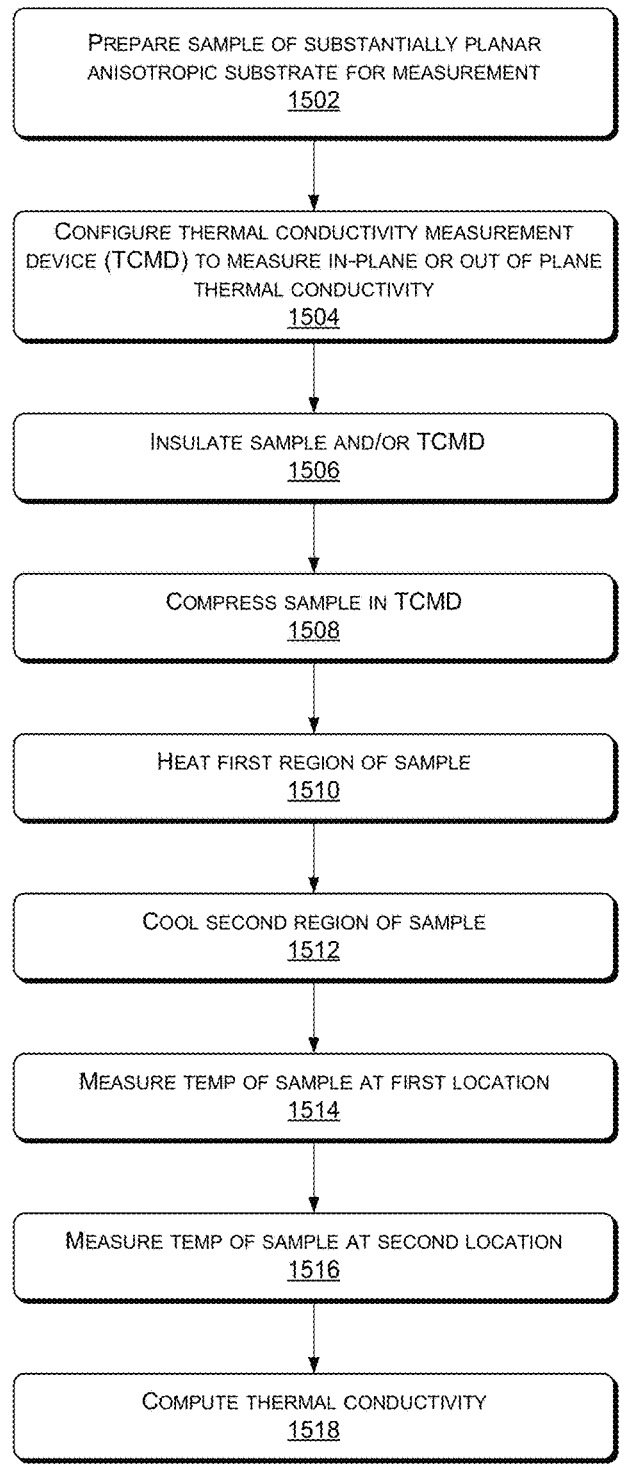
FIG. 15 is a flowchart illustrating an example method of measuring an in-plane thermal conductivity of a substantially planar anisotropic substrate.

FIG. 15 is a flowchart illustrating an example method 1500 of measuring in-plane thermal conductivity of a sample according to this disclosure. For example, the sample may comprise a substantially planar anisotropic substrate, such as a display stack or PCB. The example method 1500 is described with reference to the example thermal conductivity measurement device 400 and the system 100 for ease of explanation. However, the method 1500 is usable with other thermal conductivity measurement devices and systems.

The method 1500 includes, at block 1502, a sample may be prepared for measurement of the thermal conductivity. Preparing the sample for measurement may include cutting the material to a size that will fit in a thermal conductivity measurement device. However, the sample need not be of any particular shape. Preparing the sample may also include cleaning the sample, coating the sample with a thermal grease or other thermal interface material, or the like.

At block 1504, the thermal conductivity measurement device may be configured to test the desired thermal conductivity property. For example, one or more heating elements and/or cooling elements (e.g., cylindrical heating elements 404A and 404B, and cooling rings 406A and 406B) may be placed in a frame (e.g., frame 1400) to configure the thermal conductivity measurement device to test an in-plane thermal conductivity. Alternatively, the thermal conductivity measurement device may be configured as shown in FIG. 11 in order to test an out of plane thermal conductivity.

At block 1506, the thermal conductivity measurement device and/or sample may be insulated. For example, a surface of the sample may be insulated between a first region at which heat is to be applied to the sample and a second region at which heat is to be removed by the sample.

At block 1508 pressure may be applied by a press (e.g., jack, heavy weight, etc.) to compress or bias the heating and cooling elements firmly against the sample to be tested. Compressing the sample in the thermal conductivity measurement device may improve a contact interface between the sample and the heating and/or cooling elements.

At 1510, heat is applied to a first region of the substantially planar anisotropic substrate. Heat may be applied by one or more heating elements. The thermal conductivity measurement device is configured to apply heat to the sample so as to enforce heat transfer in the in-plane direction through a portion of the sample having a known geometry. The portion of the sample through which the heat transfer is defined by the shape and configuration of the heating and cooling elements, and is independent of the shape of the overall sample. In some examples, the heat may be applied to the first region by heating both sides of the sample using two cylindrical heating elements located on opposite sides of the sample, such as cylindrical heating elements 404A and 404.

At 1512, heat is removed from a second region of the sample (i.e., the second region is cooled) using one or more cooling elements. The second region may be spaced a distance from the first region in a direction parallel to a surface of the sample. In some examples, cooling the second region comprises cooling both sides of the sample using cooling elements, such as cooling rings 406A and 406B, disposed on opposite sides of the sample.

By applying heat to both sides of the sample, heat transfer from the first region to the second region may be made symmetric with respect to a mid-plane halfway between the top and bottom surfaces, which may simplify the calculations used to determine the in-plane thermal conductivity and improve the accuracy of the in-plane thermal conductivity measurement. However, in other examples (e.g., when testing relatively thin samples), accurate thermal conductivity measurements can be made by applying and removing heat from only one side of the sample.

At 1514, a temperature of the sample is measured at a first location proximate the first region by a first temperature sensor. At 1516, a temperature of the sample is measured at a second location proximate the second region by a second temperature sensor. In some examples, measuring the temperature at the first location comprises measuring the temperature adjacent an edge of the first region closest to the second region and measuring the temperature at the second location comprises measuring temperature adjacent an edge of the second region closest to the first region. The first and second locations may be collinear with a line extending outward from a center of the heating element(s) (e.g., cylindrical heating elements 404A and 404B, or elongated heating elements 704A and 704B). For example, the first temperature may be measured by temperature sensor A and the second temperature may be measured by temperature sensor B in FIG. 5 or in FIG. 7B.

At 1518, a thermal conductivity may be computed. In some examples, the thermal conductivity may be computed by thermal conductivity calculator 128 of the computing device 114. When an in-plane thermal conductivity is to be computed, the in-plane thermal conductivity of the sample may be computed based at least in part on the temperature at the first location, the temperature at the second location, the distance from the first region to the second region, a thickness of the substantially planar anisotropic substrate, and an amount of heat applied to the first region. In some examples, the in-plane thermal conductivity may be computed using one of equations 2 or 4 above. It is possible to use the equations described herein to compute the in-plane thermal conductivity due at least in part to the unique configurations (e.g., geometry and placement) of the heating and cooling elements of the example thermal conductivity measurement devices described herein. The configurations of the thermal conductivity measurement devices described herein enforce a uniform and predictable heat flow through a predetermined portion of a sample of material to be tested.

While the method 1500 comprises operations performed by components of thermal conductivity measurement devices (e.g., heating elements, cooling elements, frames, presses, etc.), the method 1500 should also be understood to cover operations performed by a computing device, such as computing device 114, to cause or control performance of the operations of the thermal conductivity measurement device components.

While the operations of method 1500 are described and illustrated in a particular order, the method 1500 is not limited to performance in the specified order. Rather, the order of operations may be changed, operations may be combined, and/or operations may be omitted without departing from the scope of this disclosure.

CONCLUSION

While various examples and embodiments are described individually herein, the examples and embodiments may be combined, rearranged and modified to arrive at other variations within the scope of this disclosure.

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims.

What is claimed is:

1. A thermal conductivity measurement device to measure in-plane thermal conductivity of a sample of anisotropic material having multiple heterogeneous layers, the thermal conductivity measurement device comprising:
   a frame;
   a heater coupled to the frame to heat a first region of a sample;
   a cooler coupled to the frame to cool a second region of the sample, the cooler being spaced a distance (D) from the heater in an in-plane direction, the heater and the cooler being configured to impart in-plane heat transfer in a predetermined portion of the sample;
   a first temperature sensor disposed adjacent to the heater to measure a temperature of the sample at a location adjacent to the heater; and
   a second temperature sensor disposed adjacent to the cooler to measure a temperature of the sample at a location adjacent the cooler, the second temperature sensor being spaced the distance D from the first temperature sensor.

2. The thermal conductivity measurement device of claim 1, wherein:
the heater comprises:
a first heating element coupled to the frame to contact a first side of the sample; and
a second heating element coupled to the frame to contact a second side of the sample opposite the first side of the sample; and
the cooler comprises:
a first cooling element coupled to the frame to contact the first side of the sample; and
a second cooling element coupled to the frame to contact the second side of the sample opposite the first side of the sample.

3. The thermal conductivity measurement device of claim 2, wherein:
the first heating element comprises a cylindrical resistance heater having a radius;
the second heating element comprises a cylindrical resistance heater having the radius;
the first cooling element comprises a cooling ring encircling the first cylindrical resistance heater and having an inner radius greater than the radius of the first and second cylindrical resistance heaters; and
the second cooling element comprises a cooling ring encircling the first cylindrical resistance heater and having an inner radius greater than the radius of the first and second cylindrical resistance heaters.

4. The thermal conductivity measurement device of claim 2, further comprising a temperature controller electrically coupled to the first heating element and the second heating element to regulate the first heating element and the second heating element to maintain temperatures at opposing surfaces of the sample at substantially a same temperature, to generate in-plane heat transfer that is substantially symmetric with respect to a mid-plane halfway between the opposing surfaces of the sample.

5. The thermal conductivity measurement device of claim 2, further comprising:
a first heatsink or radiator fluidly coupled to the first cooling element;
a pump fluidly coupled between the first heatsink or radiator and the first cooling element to circulate a fluid between the first heatsink or radiator and the first cooling element;
a second heatsink or radiator fluidly coupled to the second cooling element; and
a second pump fluidly coupled between the second heatsink or radiator and the second cooling element to circulate a fluid between the second heatsink or radiator and the second cooling element.

6. The thermal conductivity measurement device of claim 1, further comprising insulation disposed between the heater and the cooler to insulate against radiant heat transfer between the heater and the cooler.

7. The thermal conductivity measurement device of claim 1, further comprising a press coupled to the frame to bias the heater and the cooler against the sample.

8. The thermal conductivity measurement device of claim 1, further comprising a computing device electrically coupled to the heater, the first temperature sensor, and the second temperature sensor,
the computing device programmed to compute an in-plane thermal conductivity of the sample based at least in part on power consumed by the heater and temperatures measured by the first temperature sensor and the second temperature sensor.

9. The thermal conductivity measurement device of claim 8, wherein the computing device comprises memory storing an algorithm to compute the in-plane thermal conductivity of the sample, the algorithm being based on sizes, shapes, and relative positions of the heater and the cooler.

10. An apparatus comprising:
a frame;
a heater coupled to the frame to heat a first region of a sample;
a cooler coupled to the frame to cool a second region of the sample, the cooler being spaced a distance (D) from the heater in an in-plane direction relative to the sample;
a first temperature sensor disposed adjacent to the heater to measure a temperature of the sample at a location adjacent to the heater; and
a second temperature sensor disposed adjacent to the cooler to measure a temperature of the sample at a location adjacent the cooler, the second temperature sensor being spaced the distance D from the first temperature sensor.

11. The apparatus of claim 10, wherein:
the heater comprises:
a first heating element coupled to the frame to contact a first side of the sample; and
a second heating element coupled to the frame to contact a second side of the sample opposite the first side of the sample; and
the cooler comprises:
a first cooling element coupled to the frame to contact the first side of the sample; and
a second cooling element coupled to the frame to contact the second side of the sample opposite the first side of the sample.

12. The apparatus of claim 11, wherein:
the first heating element comprises a cylindrical resistance heater having a radius;
the second heating element comprises a cylindrical resistance heater having the radius;
the first cooling element comprises a cooling ring encircling the first cylindrical resistance heater and having an inner radius greater than the radius of the first and second cylindrical resistance heaters; and
the second cooling element comprises a cooling ring encircling the first cylindrical resistance heater and having an inner radius greater than the radius of the first and second cylindrical resistance heaters.

13. The apparatus of claim 11, further comprising a temperature controller electrically coupled to the first heating element and the second heating element to regulate the first heating element and the second heating element to maintain temperatures at opposing surfaces of the sample at substantially a same temperature, to generate in-plane heat transfer that is substantially symmetric with respect to a mid-plane halfway between the opposing surfaces of the sample.

14. The apparatus of claim 11, further comprising:
a first heatsink or radiator fluidly coupled to the first cooling element;
a pump fluidly coupled between the first heatsink or radiator and the first cooling element to circulate a fluid between the first heatsink or radiator and the first cooling element;
a second heatsink or radiator fluidly coupled to the second cooling element; and
a second pump fluidly coupled between the second heatsink or radiator and the second cooling element to circulate a fluid between the second heatsink or radiator and the second cooling element.

15. The apparatus of claim 10, further comprising a computing device electrically coupled to the heater, the first temperature sensor, and the second temperature sensor,
the computing device programmed to compute an in-plane thermal conductivity of the sample based at least in part on power consumed by the heater and temperatures measured by the first temperature sensor and the second temperature sensor.

16. The apparatus of claim 15, wherein the computing device comprises memory storing an algorithm to compute the in-plane thermal conductivity of the sample, the algorithm being based on sizes, shapes, and relative positions of the heater and the cooler.

17. A system comprising:
a thermal conductivity measurement device comprising:
a heater to heat a first region of a sample;
a cooler to cool a second region of the sample, the cooler being spaced a distance (D) from the heater in an in-plane direction relative to the sample;
a first temperature sensor disposed adjacent to the heater to measure a temperature of the sample at a location adjacent to the heater; and
a second temperature sensor disposed adjacent to the cooler to measure a temperature of the sample at a location adjacent the cooler, the second temperature sensor being spaced the distance D from the first temperature sensor; and
a computing device electrically coupled to the heater, the first temperature sensor, and the second temperature sensor, the computing device programmed to compute an in-plane thermal conductivity of the sample based at least in part on power consumed by the heater and temperatures measured by the first temperature sensor and the second temperature sensor.

18. The system of claim 17, further comprising:
a frame coupled to at least one of the heater or the cooler; and
a press coupled to the frame to bias the at least one of the heater or the cooler against the sample.

19. The apparatus of claim 11, wherein the in-plane direction is a direction parallel to at least one of the first side or the second side of the sample.

20. The system of claim 17, wherein at least one heater and at least one cooler are disposed on a same side of the sample.

* * * * *